US012683025B2

(12) United States Patent
Dosenbach et al.

(10) Patent No.: US 12,683,025 B2
(45) Date of Patent: Jul. 14, 2026

(54) SYSTEMS AND METHODS FOR MONITORING FUNCTIONAL NEUROPLASTICITY

(71) Applicants: Nico Dosenbach, St. Louis, MO (US); Dillan Newbold, St. Louis, MO (US)

(72) Inventors: Nico Dosenbach, St. Louis, MO (US); Dillan Newbold, St. Louis, MO (US)

(73) Assignee: Washington University, St. Louis, MO (US)

( * ) Notice: Subject to any disclaimer, the term of this patent is extended or adjusted under 35 U.S.C. 154(b) by 696 days.

(21) Appl. No.: 17/349,901

(22) Filed: Jun. 16, 2021

(65) Prior Publication Data

US 2021/0398678 A1     Dec. 23, 2021

Related U.S. Application Data

(60) Provisional application No. 63/039,983, filed on Jun. 16, 2020.

(51) Int. Cl.
| | |
|---|---|
| *G16H 50/20* | (2018.01) |
| *A61B 5/00* | (2006.01) |
| *A61B 5/055* | (2006.01) |
| *A61B 5/16* | (2006.01) |
| *A61B 5/31* | (2021.01) |

(Continued)

(52) U.S. Cl.
CPC ............ *G16H 50/20* (2018.01); *A61B 5/055* (2013.01); *A61B 5/165* (2013.01); *A61B 5/31* (2021.01); *A61B 5/4848* (2013.01); *A61B 5/486* (2013.01); *A61B 5/7253* (2013.01);

*A61B 5/742* (2013.01); *G01R 33/4806* (2013.01); *G16H 20/70* (2018.01)

(58) Field of Classification Search
CPC .. G16H 50/20; A61B 2576/026; A61B 5/369; A61B 5/7282; A61B 5/7264; A61B 5/31; A61B 5/4064; A61B 5/165; G01R 33/4806
See application file for complete search history.

(56) References Cited

U.S. PATENT DOCUMENTS

2018/0014772 A1* 1/2018 Dolev .................. A61B 5/4076
2021/0353205 A1* 11/2021 Fogel ...................... G06N 3/08

OTHER PUBLICATIONS

Arpan Dutta, Resting state networks in major depressive disorder, Psychiatry Research: Neuroimaging (Year: 2014).*

(Continued)

*Primary Examiner* — Amelie R Davis

(57) ABSTRACT

Systems and methods for monitoring neuroplasticity within at least one region of interest of a brain of a subject are disclosed. The method includes transforming at least one time sequence of signals indicative of neural activity into a summary parameter indicative of plasticity pulses. The method further includes evaluating the summary parameter with respect to one or more threshold values to obtain a determination of neuroplasticity within at least one region of interest of the subject. The method may be used to evaluate the efficacy of a neuroactive therapy, such as a neuroactive medication, a physical therapy, an occupational therapy or a speech therapy. The summary parameter obtained using the disclosed method may be displayed to a subject as a bio-feedback during a neurotherapy.

9 Claims, 14 Drawing Sheets
(10 of 14 Drawing Sheet(s) Filed in Color)

(51) Int. Cl.
    *G01R 33/48*         (2006.01)
    *G16H 20/70*         (2018.01)

(56)                     References Cited

OTHER PUBLICATIONS

Guerra-Carrillo et al. Resting-state fMRI: a window into human brain plasticity. Neuroscientist. Oct. 2014; 20(5):522-33 (Year: 2014).*

Zhou, F. et al. (2014) Increased Low-Frequency Oscillation Amplitude of Sensorimotor Cortex Associated with the Severity of Structural Impairment in Cervical Myelopathy. PLoS One, vol. 9, No. 8, pp. e104442.

Yaping, X. et al. (2019) Altered brain functional connectivity and correlation with psychological status in patients with unilateral pulsatile tinnitus. Neuroscience Letters, vol. 705, pp. 235-245.

Yue, X. et al. (2020) Altered intrinsic brain activity and regional cerebral blood flow in patients with chronic neck and shoulder pain. Pol J Radiol, vol. 85, pp. e155-e162.

Deng, Z. et al. (2016) Resting-state low-frequency fluctuations reflect individual differences in spoken language learning. Cortex, vol. 76, pp. 63-78.

Hu, M. et al. (2018) Differential Amplitude of Low-Frequency Fluctuations in brain networks after BCI Training with and without tDCS in Stroke. Annu Int Conf IEEE Eng Med Biol Soc, vol. 2018, pp. 1050-1053.

* cited by examiner

SUBJECT 1                    SUBJECT 2                    SUBJECT 3

SUBJECT 1

Pre                          Cast                          Post

SUBJECT 2

Pre                          Cast                          Post

SUBJECT 3

Pre                          Cast                          Post

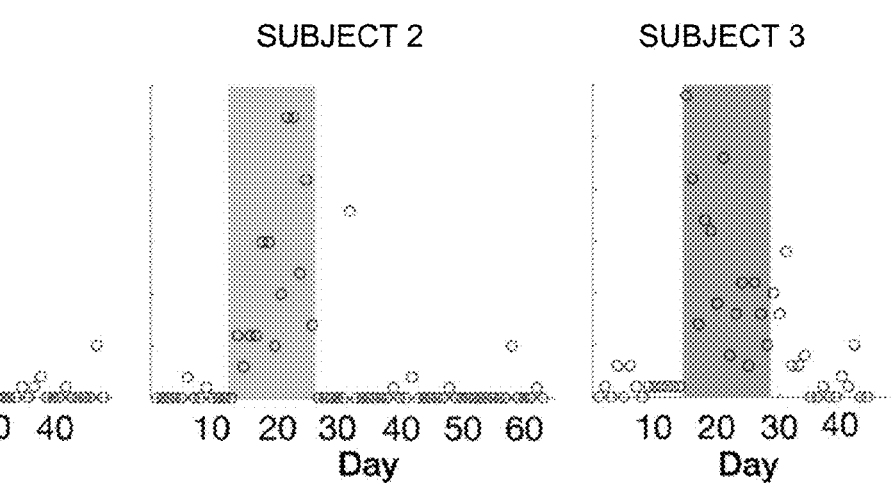
FIG. 9D
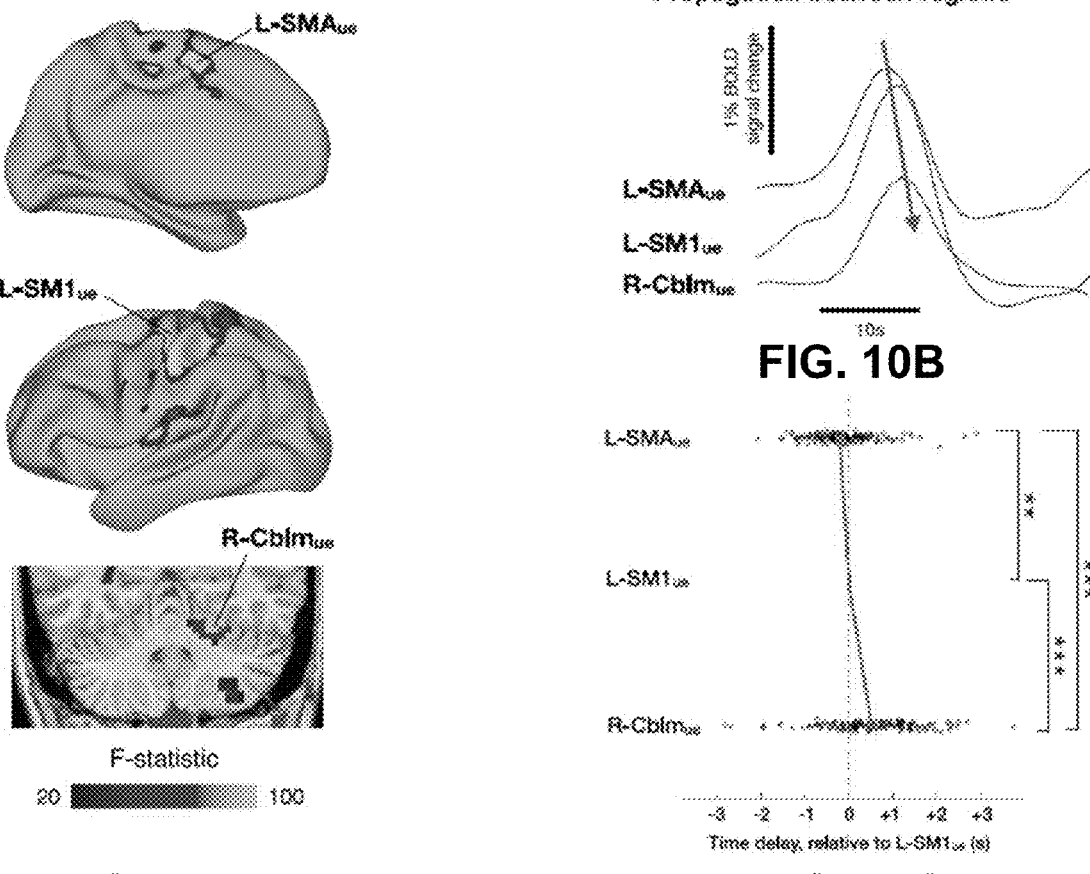
FIG. 10A
FIG. 10B
FIG. 10C

SYSTEMS AND METHODS FOR MONITORING FUNCTIONAL NEUROPLASTICITY

CROSS-REFERENCE TO RELATED APPLICATIONS

This application claims the benefit of U.S. Provisional Application No. 63/039,983 filed Jun. 16, 2020, the contents of which are incorporated by reference in its entirety.

STATEMENT REGARDING FEDERALLY SPONSORED RESEARCH OR DEVELOPMENT

This invention was made with government support under NS088590 and MH122066 awarded by the National Institutes of Health. The government has certain rights in the invention.

MATERIAL INCORPORATED-BY-REFERENCE

Not applicable.

FIELD OF THE INVENTION

The present disclosure generally relates to computer-aided systems and methods of monitoring functional neuroplasticity.

BACKGROUND OF THE INVENTION

Resting-state functional MRI (rs-fMRI) is being widely used to extract and examine the macroscale functional network organization of the human brain. There has been a great deal of excitement about using generic resting state functional connectivity (RSFC) derived from rs-fMRI data in diagnostics and prognostics for psychiatry, neurology and neurosurgery. RSFC has already found medical usage in neurosurgical planning, where it is used to delineate the motor and language networks without requiring more cumbersome task-based fMRI.

Use-driven plasticity is critical for shaping neural circuits during development, learning, and recovery from injury. Yet, the large-scale functional organization of the human brain is remarkably stable from day to day and largely robust to changes in behavioral state. Resting-state functional magnetic resonance imaging (rs-fMRI) provides a powerful means of examining human brain organization by recording spontaneous neural activity, i.e., activity not related to external stimuli or overt behaviors. Spontaneous activity consumes the vast majority of the brain's metabolic energy and is synchronized within functionally related regions, a phenomenon known as functional connectivity (FC). FC is characteristically strong between corresponding regions of the left and right hemispheres (homotopic regions) and within large-scale functional systems with distinct cognitive functions.

It has been hypothesized that FC is modulated through Hebbian-like processes, such that FC is strengthened through coactivation of brain regions. Previous attempts to induce changes in brain organization using training paradigms have shown only subtle changes in FC ($\Delta r$~0.1). In addition, prior studies relied on endpoint measurements and were therefore unable to describe the time courses of FC alterations. Developmental FC changes suggest that patterns of coactivation could be accumulated over years, but little is known about the effects of behavioral changes on brain organization over shorter time frames.

SUMMARY OF THE INVENTION

Among the various aspects of the present disclosure is the provision of systems and methods for monitoring neuroplasticity within a brain of a subject.

In one aspect, a computer-aided method of monitoring neuroplasticity within at least one region of interest of a brain of a subject is disclosed. The method includes receiving, using a computing device, at least one time sequence of signals indicative of neuroactivity within at least one region of interest within the brain of the subject. The method also includes transforming, using the computing device, the at least one time sequence of signals into a summary parameter indicative of the presence of plasticity pulses, the summary parameter comprising at least one of: a production rate of plasticity pulses, a mean amplitude of plasticity pulses, an amplitude of low frequency fluctuations, and any combination thereof. The method also includes transforming, using the computing device, the summary parameter into a determination of neuroplasticity according to a neuroplasticity rule and displaying the determination of neuroplasticity to a clinical practitioner. The determination of neuroplasticity comprises at least one of a presence of neuroplasticity, a magnitude of neuroplasticity, and a spatial extent of neuroplasticity within the brain of the subject.

In another aspect, a computer-aided method of evaluating an efficacy of a neuroactive therapy is disclosed. The method includes obtaining, using a computing device, a pre-treatment determination of neuroplasticity using the method of any preceding claim prior to administration of a neuroactive therapy. The method also includes obtaining, using the computing device, at least one post-treatment determination of neuroplasticity using the method of any preceding claim at least once after administration of the neuroactive therapy. The method also includes determining, using the computing device, the efficacy of the neuroactive therapy based on the pretreatment determination of neuroplasticity and the at least one post-treatment determination of neuroplasticity, wherein the efficacy of the neuroactive therapy is proportional to an increase in post-treatment neuroplasticity relative to pre-treatment neuroplasticity.

In an additional other aspect, a computer-aided method of screening a neuroactive medication for use in a therapy is disclosed. The method includes obtaining, using a computing device, a pre-treatment determination of neuroplasticity using the method of any preceding claim prior to administration of the neuroactive medication to a subject. The method also includes obtaining, using the computing device, at least one post-treatment determination of neuroplasticity using the method of any preceding claim at least once after administration of the neuroactive medication to the subject. The method also includes selecting, using the computing device, the neuroactive medication for a therapy if the at least one post-treatment determination of neuroplasticity indicates higher neuroplasticity relative to the pre-treatment determination of neuroplasticity In yet another additional aspect, a computer-aided method of providing a biofeedback to a subject undergoing a neuroactive therapy is disclosed. The method includes monitoring, using a computing device, a determination of neuroplasticity using the disclosed methods herein during administration of the neuroactive therapy to the subject. The method further includes displaying, using the computing device, the determination of neuroplasticity to the subject as a biofeedback.

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

The following drawings illustrate various aspects of the disclosure. Those of skill in the art will understand that the drawings, described below, are for illustrative purposes only. The drawings are not intended to limit the scope of the present teachings in any way.

FIG. 9D is a series of graphs summarizing the number of disuse pulses detected during each day of the experiment for subjects 1, 2, and 3. All subjects showed significantly more pulses per session during the cast period than during the pre-period. (Subject 1: p=0.002; Subject 2: p<0.001; Subject 3: p<0.001).

FIG. 10A contains a series of whole-brain pulse maps summarizing whole-brain analysis of variance (ANOVA) of disuse pulses in subject 2. In addition to L-SM1ue, pulses also occur in the left supplementary motor area (L-SMAue) and right cere-bellum (R-Cblmue).

FIG. 10B is a graph summarizing example pulses in L-SMAue, L-SM1ue and R-Cblmue. Note the temporal offset of peaks in each region.

FIG. 100 is a graph summarizing time delays (relative to L-SM1ue) of all pulses in each region for subject 2. Blue lines indicate median delay±SEM in each region. Pulses occurred first in L-SMAue, then L-SM1ue, and finally in R-Cblmue. Pulse times were determined by parabolic interpolation of cross-correlations with the mean pulse time series. p<0.01. *p<0.001.

DETAILED DESCRIPTION OF THE INVENTION

Figure 1:
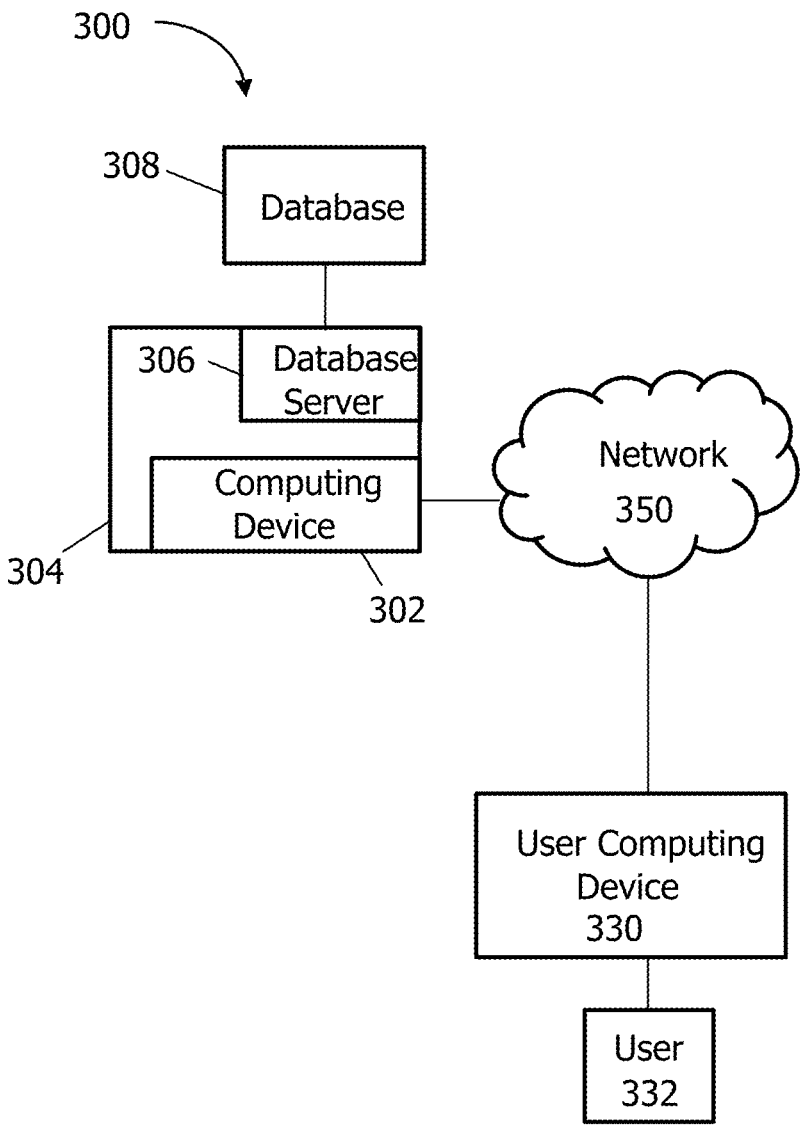
FIG. 1 is a block diagram schematically illustrating a system in accordance with one aspect of the disclosure.

The systems and methods of the present disclosure make use of the discovery of large, spontaneous pulses of neural activity, different from standard rs-fMRI and RSFC signals, that arise in the setting of brain disuse and network plasticity. In various aspects, a novel analysis stream is used to detect and measure these spontaneous plasticity pulses in individual patients. As described in the examples below, these plasticity pulses are a marker for functional network reorganization that may appear several days after the brain starts reorganizing itself. The plasticity pulses subside after functional network reorganization is completed.

Unlike existing methodologies, such as rs-fMRI and RSFC methodologies, plasticity pulses are easily detectable in single subjects using analytics as disclosed herein. Without being limited to any particular theory, the analytics derived from detected plasticity pulses are related to successful functional network reorganization and consequently are predictive of better outcomes following any type of brain injury, including, but not limited to, stroke, TBI, and neurosurgery. Thus, the disclosed plasticity pulse detection methods herein may be used for outcome prognosis after brain injury. The disclosed method may also be used as a measure of efficacy in the development of neuroactive medications aimed at increasing brain plasticity and therefore boosting recovery from various forms of brain injury. In some aspects, the frequency and amplitude of spontaneous plasticity pulses detected using the disclosed method may function as a non-invasive index of how successful any compound is at boosting brain plasticity and recovery. In other aspects, the frequency and amplitude of spontaneous plasticity pulses may be used as a biomarker for new learning and/or the progress of physical, occupational and speech therapy. In these other aspects, realtime neurobiofeedback with plasticity pulses may be included as part of rehabilitative therapies Plasticity pulses detected using the disclosed method may also be used to help target neuromodulatory interventions including, but not limited to, TMS, tDCS, and DBS. Realtime neurobiofeedback about plasticity pulses could be included as part of rehabilitative therapies. In other additional aspects, plasticity pulses detected during learning and development may be used to delineate various developmental critical periods in humans In various aspects, the plasticity pulses may be detected using the disclosed method to analyze at least one time series of signals indicative of neural activity within at least one region of interest within the brain. In various aspects, the time series of signals may be obtained using any known means including, but not limited to, BOLD rs-fMRI, EEG, or single-unit recordings such as microelectrodes. In various other aspects, the disclosed method may be used to detect plasticity pulses within the brains of a variety of subjects including, but not limited to, humans and animal models such as mice, rats, and non-human primates. Nothing similar to these plasticity pulses has ever been described before, in any animal, using any methodology. They hold great promise for stroke and TBI care, neuromodulation and neuroactive drug development.

Neuroplasticity, or alternatively brain plasticity, as used herein, refers to the ability of the brain to undergo structural or physiological changes. Without being limited to any particular theory, neuroplasticity is thought to optimize the neural networks during phylogenesis, ontogeny and physiological learning, as well as in response to a brain injury. Behavior, environmental stimuli, thought, meditation and emotions may also cause neuroplastic change through activity-dependent plasticity. Activity dependent neuroplasticity is thought to play a role in a variety of neural processes including, but not limited to, healthy development, learning, memory, and recovery from brain damage. Neuroplasticity may occur in response to previous activity (activity-dependent plasticity) to acquire memory or in response to malfunction or damage of neurons (reactive plasticity) to compensate a pathological event. In the latter case, neuroplasticity may facilitate the transfer of neural functions from one part of the brain to another part of the brain based on the demand to produce recovery of behavioral or physiological processes.

As described in the examples, brain plasticity was induced in humans by placing casts on one dominant upper extremity for 2 weeks and changes in functional connectivity were tracked using daily 30-min scans of resting-state functional MRI (rs-fMRI). Casting caused cortical and cerebellar regions controlling the disused extremity to functionally disconnect from the rest of the somatomotor system, while internal connectivity within the disused sub-circuit was maintained. Functional disconnection was evident within 48 h, progressed throughout the cast period, and reversed after cast removal. During the cast period, large, spontaneous pulses of activity propagated through the disused somatomotor sub-circuit. The results of the experiments described in the examples indicate that the adult brain seems to rely on regular use to maintain its functional architecture. Disuse-driven spontaneous activity pulses may help preserve functionally disconnected sub-circuits.

In various aspects, the disclosed method may be implemented using a computing system or computing device. FIG. 1 depicts a simplified block diagram of the system for implementing the computer-aided methods of monitoring neuroplasticity described herein. As illustrated in FIG. 1, the computing device 300 may be configured to implement at least a portion of the tasks associated with the disclosed methods of monitoring neuroplasticity described herein. The computer system 300 may include a computing device 302. In one aspect, the computing device 302 is part of a server system 304, which also includes a database server 306. The computing device 302 is in communication with a database 308 through the database server 306. The computing device 302 is communicably coupled to a user computing device 330 through a network 350. The network 350 may be any network that allows local area or wide area communication between the devices. For example, the network 350 may allow communicative coupling to the Internet through at least one of many interfaces including, but not limited to, at least one of a network, such as the Internet, a local area network (LAN), a wide area network (WAN), an integrated services digital network (ISDN), a dial-up-connection, a digital subscriber line (DSL), a cellular phone connection, and a cable modem. The user computing device 330 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices.

Figure 2:
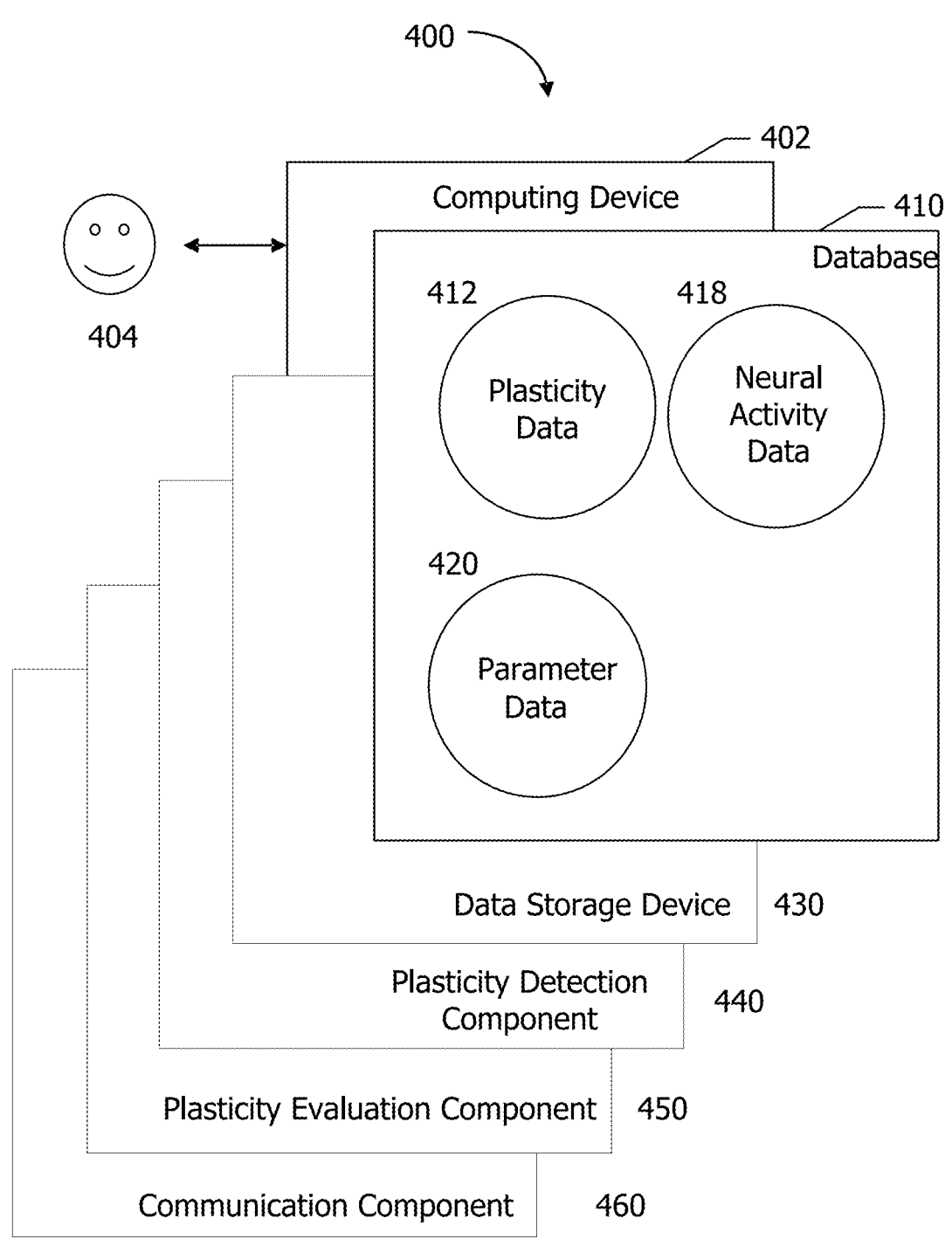
FIG. 2 is a block diagram schematically illustrating a computing device in accordance with one aspect of the disclosure.

In other aspects, the computing device 302 is configured to perform a plurality of tasks associated with disclosed computer-aided method of monitoring neuroplasticity. FIG. 2 depicts a component configuration 400 of computing device 402, which includes database 410 along with other related computing components. In some aspects, computing device 402 is similar to computing device 302 (shown in FIG. 1). A user 404 may access components of computing device 402. In some aspects, database 410 is similar to database 308 (shown in FIG. 1).

In one aspect, database 410 includes neural activity data 418, parameter data 420, and plasticity data 412. Non-limiting examples of suitable parameter data 420 include any values of parameters defining the implementation of the disclosed method of method of monitoring neuroplasticity disclosed herein including, but not limited to, parameters defining threshold values used to detect plasticity pulses, numbers of plasticity pulses, amplitudes of plasticity pulses, and any other parameters defining any other aspect of implementing the method of plasticity monitoring as described herein. In one aspect, the plasticity data 412 includes any values defining the summary parameters indicative of the presence of plasticity pulses, the determination of neuroplasticity, and any other parameter describing the plasticity detected using the disclosed methods as described herein. In one aspect, the neural activity data 418 includes any of the at least one time series values of signals indicative of neural activity within at least one region of interest within the brain of a subject.

Computing device 402 also includes a number of components that perform specific tasks. In the example aspect, computing device 402 includes data storage device 430, plasticity detection component 440, plasticity evaluation component 450, and communication component 460. Data storage device 430 is configured to store data received or generated by computing device 402, such as any of the data stored in database 410 or any outputs of processes implemented by any component of computing device 402.

The plasticity detection component 440 enables the detection of plasticity pulses using the disclosed method as described herein. In various aspects, the plasticity detection component 440 is configured to transforming at least one time sequence of signals indicative of neural activity into a summary parameter indicative of the presence of plasticity pulses. Non-limiting examples of the summary parameter include at least one of: a production rate of plasticity pulses, a mean amplitude of plasticity pulses, an amplitude of low frequency fluctuations, and any combination thereof. The plasticity evaluation component 450 enables the transformation of the summary parameter into a determination of neuroplasticity according to a neuroplasticity rule as described herein.

Communication component 460 is configured to enable communications between computing device 402 and other devices (e.g. user computing device 330 shown in FIG. 1) over a network, such as network 350 (shown in FIG. 1), or a plurality of network connections using predefined network protocols such as TCP/IP (Transmission Control Protocol/Internet Protocol).

Figure 3:
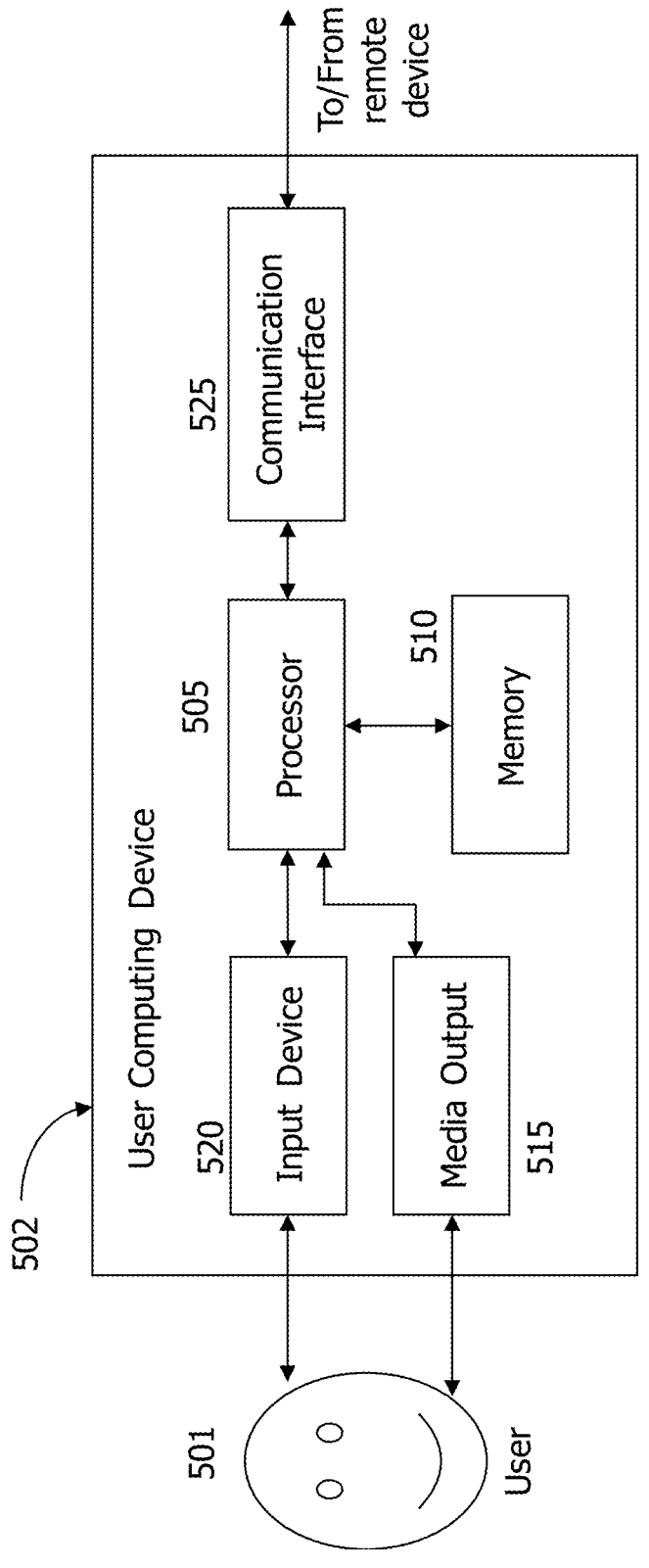
FIG. 3 is a block diagram schematically illustrating a remote or user computing device in accordance with one aspect of the disclosure.

FIG. 3 depicts a configuration of a remote or user computing device 502, such as user computing device 330 (shown in FIG. 1). Computing device 502 may include a processor 505 for executing instructions. In some aspects, executable instructions may be stored in a memory area 510. Processor 505 may include one or more processing units (e.g., in a multi-core configuration). Memory area 510 may be any device allowing information such as executable instructions and/or other data to be stored and retrieved. Memory area 510 may include one or more computer-readable media.

Computing device 502 may also include at least one media output component 515 for presenting information to a user 501. Media output component 515 may be any component capable of conveying information to user 501. In some aspects, media output component 515 may include an output adapter, such as a video adapter and/or an audio adapter. An output adapter may be operatively coupled to processor 505 and operatively coupleable to an output device such as a display device (e.g., a liquid crystal display (LCD), organic light emitting diode (OLED) display, cathode ray tube (CRT), or "electronic ink" display) or an audio output device (e.g., a speaker or headphones). In some aspects, media output component 515 may be configured to present an interactive user interface (e.g., a web browser or client application) to user 501.

In some aspects, computing device 502 may include an input device 520 for receiving input from user 501. Input device 520 may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of media output component 515 and input device 520.

Computing device 502 may also include a communication interface 525, which may be communicatively coupleable to a remote device. Communication interface 525 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WI MAX)).

Stored in memory area 510 are, for example, computer-readable instructions for providing a user interface to user 501 via media output component 515 and, optionally, receiving and processing input from input device 520. A user interface may include, among other possibilities, a web browser and client application. Web browsers enable users 501 to display and interact with media and other information typically embedded on a web page or a website from a web server. A client application allows users 501 to interact with a server application associated with, for example, a vendor or business.

Figure 4:
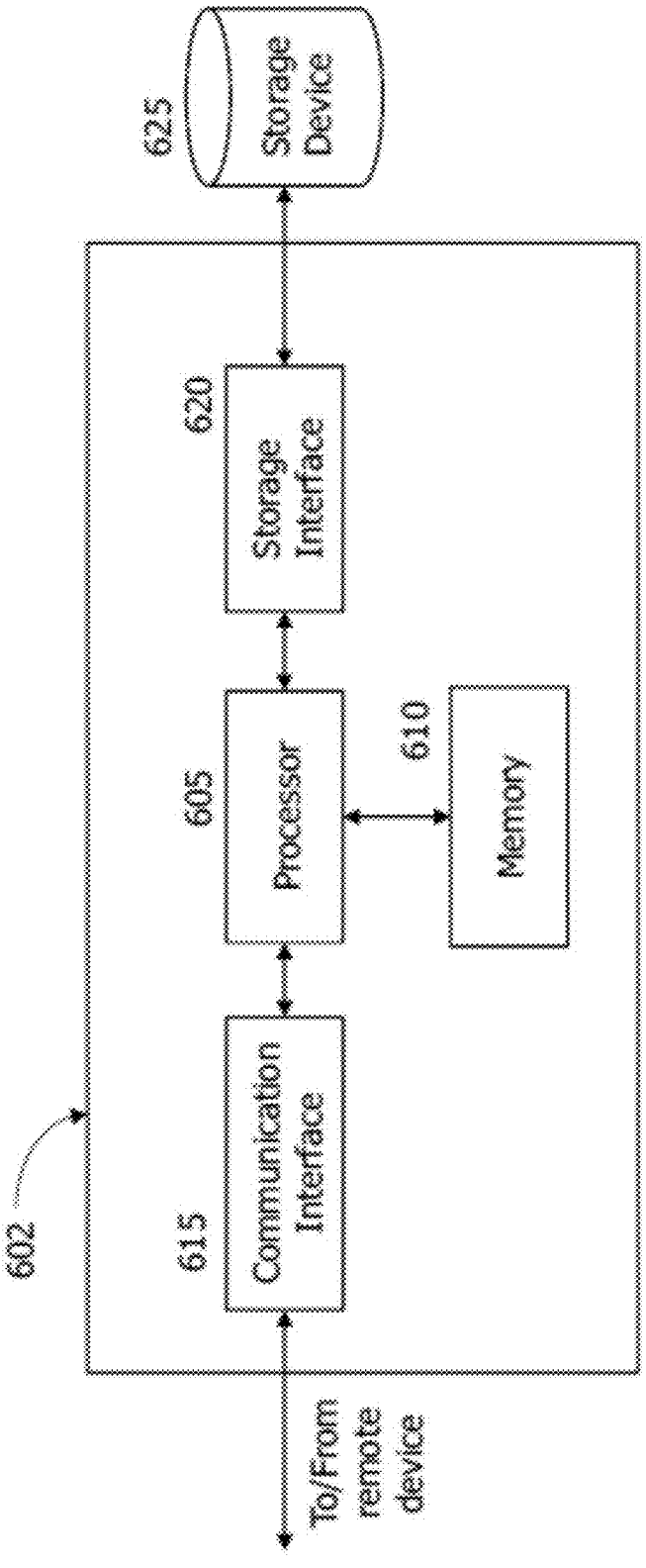
FIG. 4 is a block diagram schematically illustrating a server system in accordance with one aspect of the disclosure.

FIG. 4 illustrates an example configuration of a server system 602. Server system 602 may include, but is not limited to, database server 306 and computing device 302 (both shown in FIG. 1). In some aspects, server system 602 is similar to server system 304 (shown in FIG. 1). Server system 602 may include a processor 605 for executing instructions. Instructions may be stored in a memory area 625, for example. Processor 605 may include one or more processing units (e.g., in a multi-core configuration).

Processor 605 may be operatively coupled to a communication interface 615 such that server system 602 may be capable of communicating with a remote device such as user computing device 330 (shown in FIG. 1) or another server system 602. For example, communication interface 615 may receive requests from user computing device 330 via a network 350 (shown in FIG. 1).

Processor 605 may also be operatively coupled to a storage device 625. Storage device 625 may be any computer-operated hardware suitable for storing and/or retrieving data. In some aspects, storage device 625 may be integrated in server system 602. For example, server system 602 may include one or more hard disk drives as storage device 625. In other aspects, storage device 625 may be external to server system 602 and may be accessed by a plurality of server systems 602. For example, storage device 625 may include multiple storage units such as hard disks or solid-state disks in a redundant array of inexpensive disks (RAID) configuration. Storage device 625 may include a storage area network (SAN) and/or a network attached storage (NAS) system.

In some aspects, processor 605 may be operatively coupled to storage device 625 via a storage interface 620.

Storage interface 620 may be any component capable of providing processor 605 with access to storage device 625. Storage interface 620 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 605 with access to storage device 625.

Memory areas 510 (shown in FIG. 3) and 610 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and nonvolatile RAM (NVRAM). The above memory types are example only, and are thus not limiting as to the types of memory usable for storage of a computer program.

The computer systems and computer-aided methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to images or frames of a video, object characteristics, and object categorizations. Data inputs may further include sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a region within a medical image (segmentation), categorization of a type of motion, a diagnosis based on motion of an object, motion analysis of an object, and trained model parameters ML outputs may further include: speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: genetic algorithms, linear or logistic regressions, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, adversarial learning, and reinforcement learning.

The methods and algorithms of the invention may be enclosed in a controller or processor. Furthermore, methods and algorithms of the present invention, can be embodied as a computer implemented method or methods for performing such computer-implemented method or methods, and can also be embodied in the form of a tangible or non-transitory computer readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general-purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

To demonstrate and validate the method of monitoring brain plasticity, the following experiments were conducted.

Figures 5A, 5B, 5C:
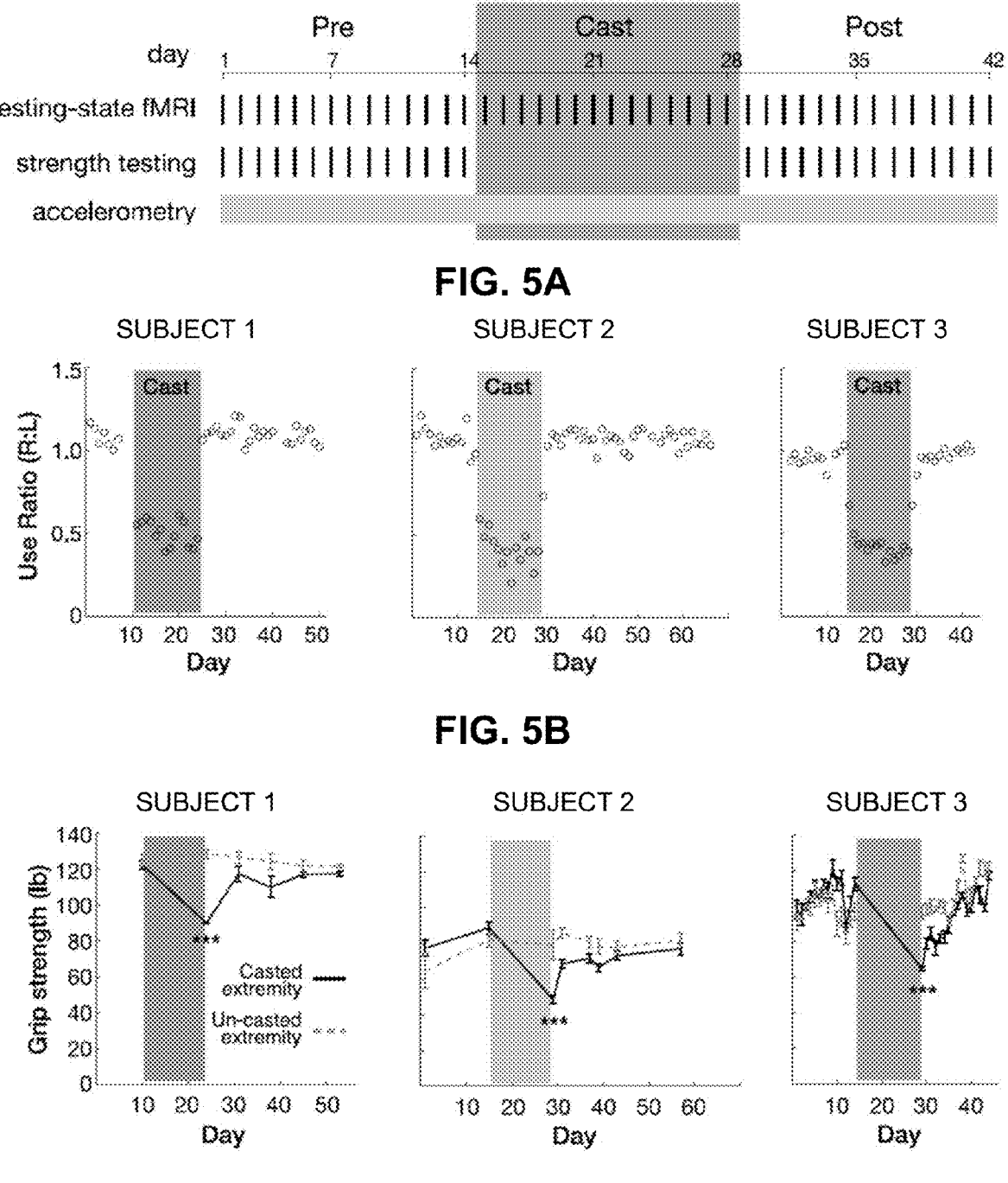
FIG. 5A is a schematic diagram illustrating an experimental design.
FIG. 5B is a series of graphs summarizing daily accelerometry data readings from both wrists of three experimental subjects, plotted as use ratios (R/L use counts). Use count=seconds each day when RMS acceleration>0.16 m/s². Use counts decreased by 41%, 55%, and 46% after subjects 1, 2, and 3, respectively were fitted with casts.
FIG. 5C is a series of graphs summarizing grip strength of the subjects of FIG. 5B, grip strength dynamometry readings decreased by 27%, 42%, and 39% for subjects 1, 2, and 3 immediately after cast removal.

To induce FC changes in human participants, we adopted an approach used in classic animal plasticity studies, which imposes sensory or motor deprivation (e.g., monocular deprivation, deafferentation, limb constraint) in a small number of intensively studied. We casted the dominant upper extremity of three adult participants (Subjects 1, 2, and 3) for 2 weeks and tracked changes in FC over 6-9 weeks using daily 30-min rs-fMRI scans (21-32 h of rs-fMRI/participant, 152 scans total; FIG. 5A). This highly sampled, longitudinal approach allowed us to measure disuse-driven plasticity in each individual and replicate results across all participants.

Methods

Human Participants

Experimental subjects were three healthy, adult volunteers. All denied recent injuries of the dominant upper extremity and any contraindications to MRI (e.g., metallic implants, claustrophobia). Because of the large amount of data collected, we were able to analyze each subjects individually, allowing us to test all hypotheses in triplicate. The first subject was a 35-year-old male, the second subject was a 25-year-old female, and the third subject was a 27-year-old male. All participants were right handed, as assessed by the Edinburgh Handedness Inventory (subject 1: +100, right-handed; subject 2: +91, right-handed; subject 3: +60, right-handed). Participants provided informed consent for all aspects of the study and were paid for their participation.

Experimental Intervention

Constraint of the dominant upper extremity was achieved by fitting each participant with a fiberglass cast that extended from just below the shoulder to past the fingertips. Casts contained an inner layer of Delta-Dry water-resistant padding (BSN Medical, Luxembourg) that provided a comfortable layer of cushioning permitting airflow; thus, participants could bathe without developing skin irritation. Extra padding was applied around the ulnar styloid process, olecranon and antecubital fossa. A strong outer shell was constructed from Delta-Lite Plus fiberglass casting tape. Tape was applied with the elbow bent at a natural angle (approximately 95°), the wrist slightly extended, the fingers slightly flexed, and the thumb extended. Casts were constructed by an Occupational Therapist specially trained in therapy involving casting. All participants were fit with a temporary cast several days before the two-week casting period to practice achieving a comfortable position; practice casts were removed after about 10 minutes. In subject 3, the cast was remade after one day to correct uncomfortable finger position. All casts were removed using a specialized, oscillating blade saw that cuts fiberglass without harming the underlying skin.

In order to test for any effects of wearing casts during scans, we cut the casts from the original experiment in half along their long axes, applied felt to the inside surfaces and all cut edges, and added Velcro fasteners to create casts that could be easily applied and removed at the start and end of scanning. Participants wore removable casts during half of the rs-fMRI sessions acquired during a control experiment but did not wear these casts during daily activities.

Activity Monitoring

Behavior during normal daily life was assessed using accelerometers worn on each wrist. All participants wore a wGT3X-BT accelerometer (Actigraph, Pensacola) on each wrist throughout the day and night for the full duration of the experiment. The only times participants removed their accelerometers were during daily MRI scans. The accelerometers recorded acceleration along three orthogonal dimensions with a sampling rate of 30 Hz.

Strength Testing

Grip strength was measured with a Jamar Smart Hand Digital Dynamometer (Patterson Medical, Warrenville). Participants were in-structed to form a closed first around a handle on the dynamometer, keeping the arm at the side with the elbow bent at 90°, and squeeze as tightly as possible. Maximal force was recorded in pounds. This was repeated for each hand in triplicate at each measurement time point (FIG. 5C).

Fine Motor Testing

Fine motor function of each upper extremity was assessed using the Purdue pegboard task. Participants were instructed to use one hand to pick up small (approximately 1 inch) metal pegs one at a time from a bin and insert them into a row of small holes on a pegboard. Participants were given 30 seconds to insert as many pegs as possible. The task was then repeated with the other hand. This task was repeated in triplicate at each assessment.

MRI Acquisition

Figure 9A:
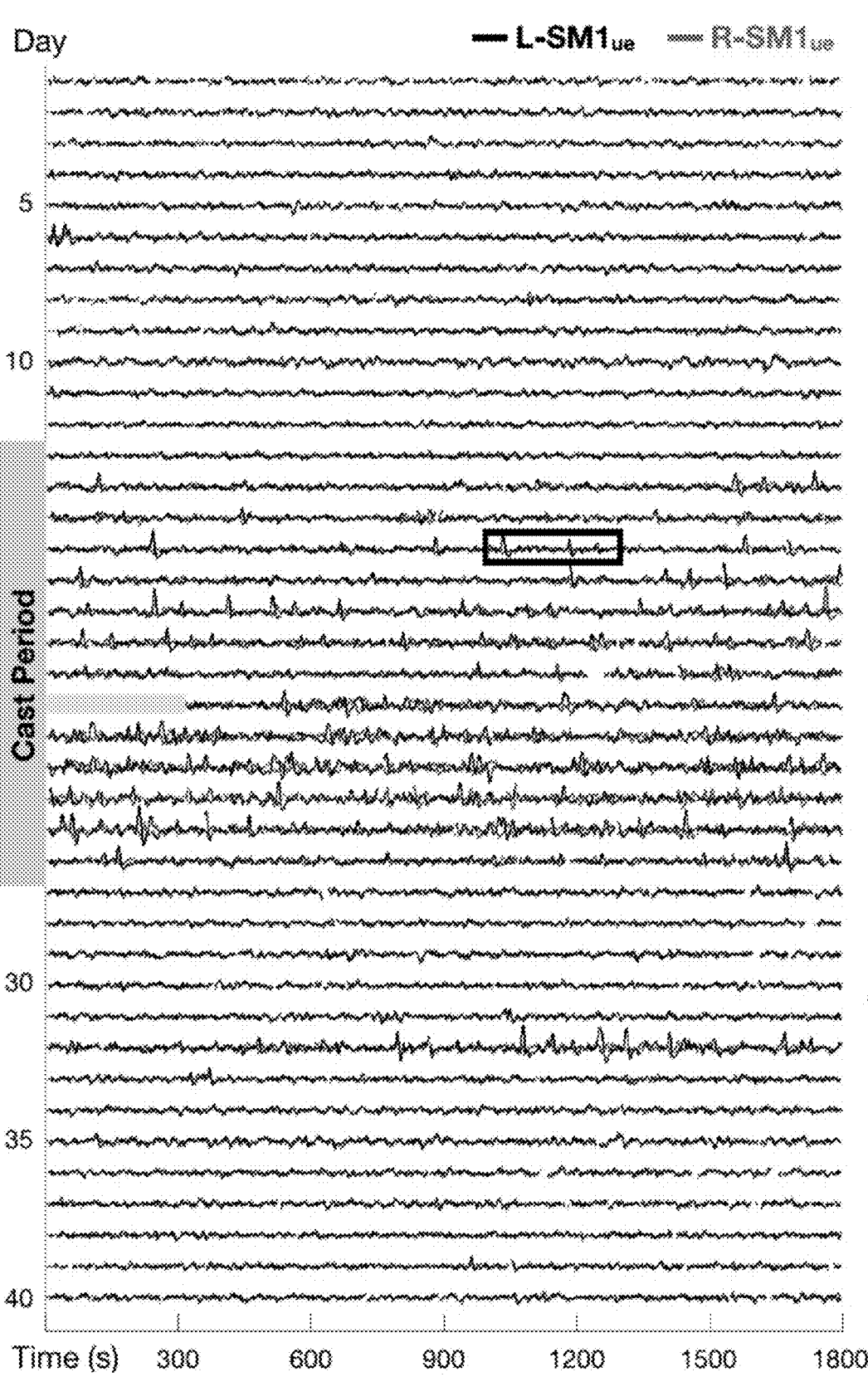
FIG. 9A is a graph of resting-state functional MRI (rs-fMRI) signals from left and right primary somatomotor cortex (L-SM1ue and R-SM1ue) before, during, and after casting in Subject 2. During the cast period, large pulses occur in L-SM1ue. Data for first 5 min of scan 21 are unavailable (gray bar).

Participants were scanned every day of the experiment, for 42-64 consecutive days, except for rare days when the scanner or the participant was unavailable. Imaging was performed at a consistent hour of the day to minimize diurnal effects in functional connectivity. Every session included a 30-minute resting-state blood oxygen level-dependent (BOLD) fMRI scan, during which participants were instructed to hold still and look at a white fixation crosshair presented on a black background. During one scan (subject 2, scan 21), the fixation crosshair was not presented until 5 minutes into the scan, so these 5 minutes of data were excluded from further processing (denoted as grey bar in FIG. 9A). Head motion was tracked in real time using Framewise Integrated Real-time MRI Monitoring software (FIRMM). An eye-tracking camera (EyeLink, Ottawa) was used to monitor participants for drowsiness. Some sessions prior to casting included motor tasks, during which participants were instructed to move their left hand, right hand, left foot, right foot, or tongue in a block design cued by visual stimuli. Two 4-minute runs of this task were completed during each task session.

Hand Movement Monitoring

Hand movements during rs-fMRI scans were tracked using a highly sensitive pneumatic bladder (Siemens, Munich), originally designed for tracking respiratory movements. This bladder was inserted into the end of the cast, along the palmar surface of the fingers during rs-fMRI scans. Instructing the participant to make very small hand movements during a test run confirmed that the bladder was extremely sensitive to movements at the finger joints, wrist, elbow and shoulder. Additionally, although the bladder was inserted inside the cast, we were still able to detect respiration.

Analysis of Accelerometry Data

Data from wrist-based accelerometers were transferred off of the devices during MRI scans and down sampled to 1 Hz. All analyses were based on a root mean square (RMS) of the three acceleration directions. Use counts were calculated as the number of seconds per day when the RMS acceleration exceeded a noise threshold of 10 accelerometer units (1 accelerometer unit=0.016 m/s$^2$). Periods of sleep were detected as blocks of 15 minutes or more with a use count below 100. "% Time Moving" was calculated as the daily use count normalized by the total number of waking seconds recorded each day. Use ratios reported in FIG. 5B were calculated as the ratio of use counts for the left and right upper extremities.

MR Image Processing

Structural images (T1- and T2-weighted) were corrected for gain field inhomogeneity using FSL Fast, and aligned to the 711-2B implementation of Talairach atlas space using the 4dfp MRI processing software package (https://readthedocs.org/projects/4dfp/). The 711-2B template conforms to the 1988 Talairach atlas. Relative to MN1152, 711-2B space is about 5% smaller and 2° anteriorly rotated about the ear-to-ear axis. Mean T1- and T2-weighted images (T1w and T2w) were computed by coregistration and averaging multiple acquisitions. The mean T1w for each participant was run through the FreeSurfer pipeline (version 5.3) to generate an anatomical segmentation and 3D surface models of the cerebral cortex.

fMRI processing followed an existing pipeline. Briefly, preprocessing included temporal interpolation to correct for slice time differences, correction of intensity differences between odd and even slices and rigid-body correction for head movement. Atlas transformation of the functional data was computed as a composition of transforms: native space mean functional image/T2w/T1w/atlas representative template. The functional data were resampled in atlas space in one step including correction for susceptibility inhomogeneity-related distortion.

Denoising was accomplished by regression of nuisance time series following a CompCor-like strategy. Regressors included the 6 rigid parameters derived by retrospective motion correction, the global signal averaged over the brain, and orthogonalized waveforms extracted from the ventricles, white matter and extra-cranial tissues (excluding the eyes). Frame censoring (scrubbing) was computed on the basis of both frame-wise displacement (FD) and variance of derivatives (DVARS) measures with thresholds set individually for each participant. Rigid-body motion parameters were low-pass filtered (<0.1 Hz) prior to FD computation to remove respiratory artifacts in head-motion estimates. Grayordinate image intensity plots were visually checked to confirm artifact reduction. The data then were temporally bandpass filtered prior to nuisance regression, retaining frequencies between 0.005 Hz and 0.1 Hz. Censored frames were replaced by linearly interpolated values prior to filtering and re-censored afterward.

Preprocessed functional data (BOLD time series) were extracted from the cerebral cortex and cerebellum using FreeSurfer-based segmentations and cortical surface models. Cortical data were projected onto a 2D surface (generated by FreeSurfer) using tools distributed as part of the Human Connectome Workbench software package. As previously described, cortical projection involves selecting voxels that fall between two surface models fit to the inner and outer surfaces of the cortex and interpolating between these voxels to project BOLD data from each cortical hemisphere to an approximately 164,000-vertex 2D surface. Surface projected data are then downsampled to approximately 32,000-vertices and geodesically smoothed using a 2-dimensional 6-mm full-width half max (FWHM) smoothing kernel. Cerebellar voxels were kept in volume space and smoothed using a 3-dimensional 4.7 mm FWHM kernel.

ROI Selection

Figures 6A, 6B, 6C, 6D:
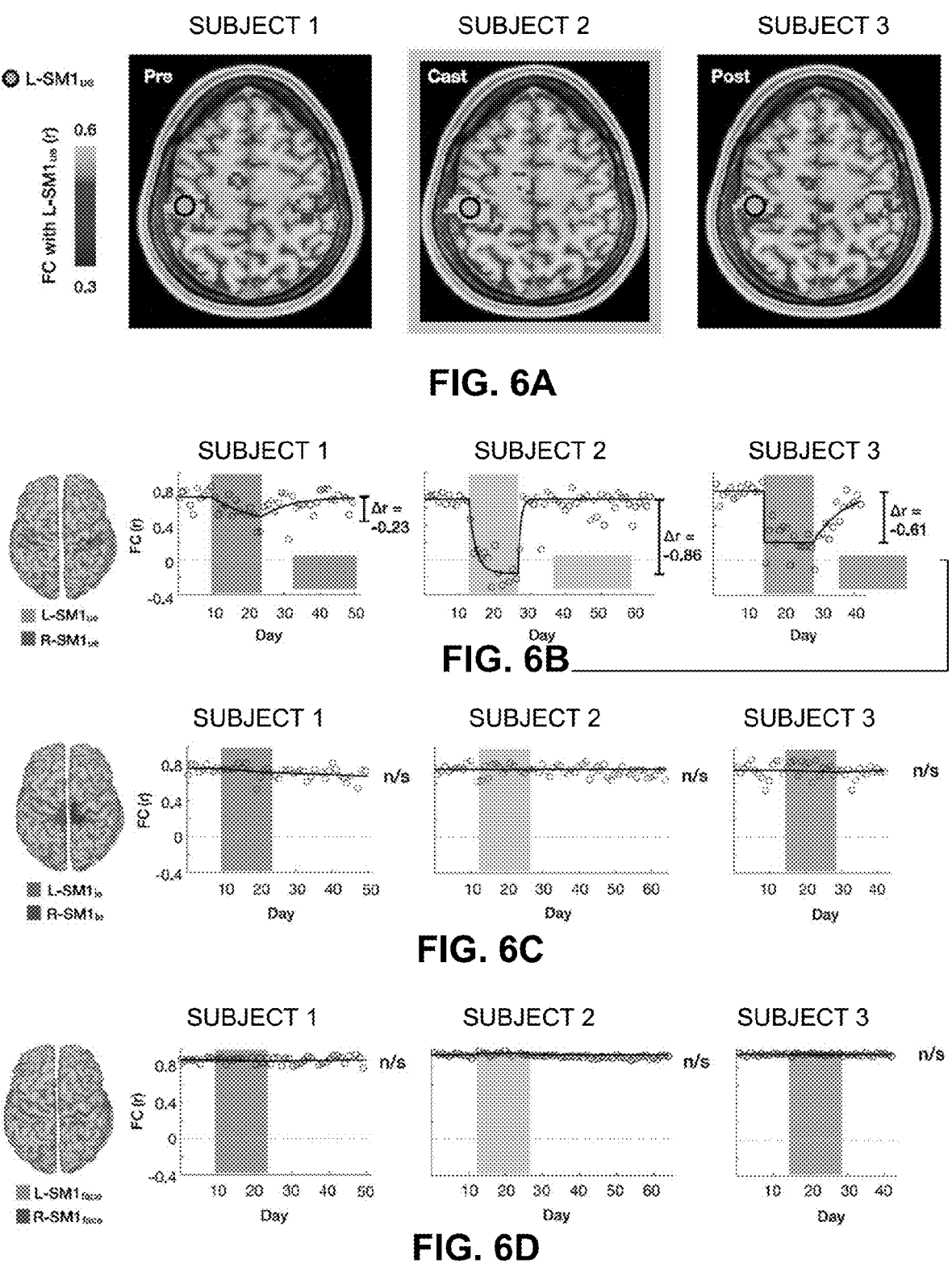
FIG. 6A contains a series of seed maps showing functional connectivity (FC) of each voxel with the left primary somatomotor cortex (L-SM1ue) during scans acquired before, during, and after casting (Pre, Cast, Post) in subject 3 of FIGS. 5B and 5C.). The L-SM1ue region of interest (ROI) was defined using task functional MRI.
FIG. 6B contains a series of graphs summarizing the daily time course of FC between L-SM1ue and R-SM1ue for the three subjects of FIGS. 5B and 5C; Ar values are based on a time-varying exponential decay model (black lines, $d_r/d_t = \alpha(r_\infty - r)$; FC decreases were significant for all subjects.
FIG. 6C contains a series of graphs summarizing the daily time course of FC in the lower extremity regions of the left and right somatomotor cortex for the three subjects of FIGS. 5B and 5C.
FIG. 6D contains a series of graphs summarizing the daily time course of FC in the face regions of the left and right somatomotor cortex for the three subjects of FIGS. 5B and 5C.

Most analyses utilized individual-specific task-defined regions of interest (ROIs). Task-defined ROIs were selected using an auto-mated analysis of task fMRI data, as previously described. For each movement in the motor task (hand, tongue or foot movement), we selected ROIs inside of two anatomical regions, which were automatically labeled by FreeSurfer: the primary somatomotor cortex (pre- and post-central gyri) and the superior half of the cerebellum. To select ROIs within each anatomical region, we first located the vertex/voxel showing maximal task synchrony during the motor task and then grew the ROI to a preset size (400 vertices in the somatomotor cortex, 40 voxels in the cerebellum) by selecting neighboring vertices/voxels in descending order of task synchrony. ROIs for an example participant (subject 3) are shown in FIGS. 6B, 6C, and 6D.

Figures 7A, 7B:
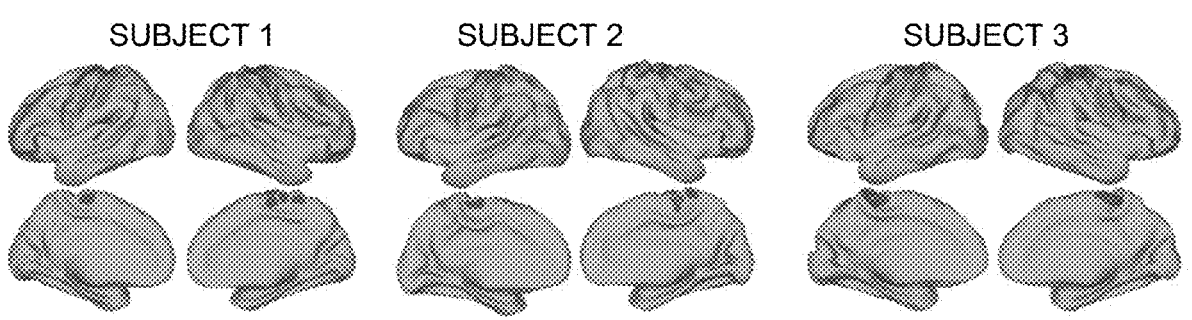
FIG. 7A contains a series of regions of interest (ROIs) in the lower-extremity (green), upper-extremity (cyan/blue), and face (orange) subdivisions of the somatomotor system for the experimental subjects of FIGS. 5B and 5C, ROIs were selected using a functional connectivity gradient-based approach.
FIG. 7B contains a series of spring-embedded graph representation of the somatomotor system before, during, and after casting for the three subjects of FIG. 7A. The disused region (L-SM1ue) separated from the remainder of the somatomotor cortex during the cast period but remained internally connected.
Figure 7C:
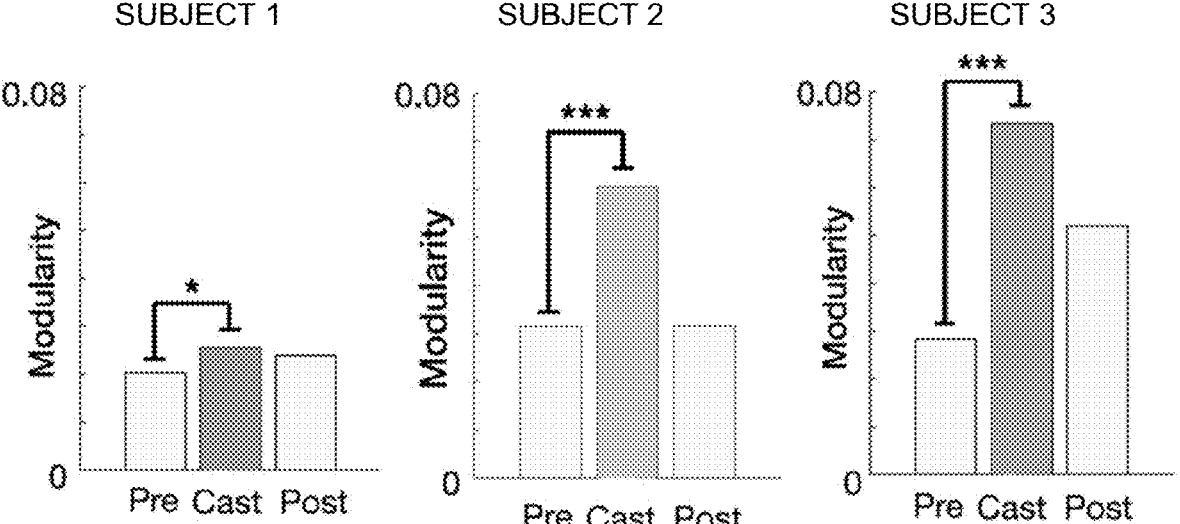
FIG. 7C contains a series of graphs summarizing the modularity quantifying the degree of dissociation between L-SM1ue and the rest of the somatomotor cortex for the three subjects of FIG. 7A. All participants showed increased modularity during the cast period. *p<0.05; ***p<0.001.

The graph-theoretic analyses shown in FIGS. 7B and 7C required multiple ROIs per somatomotor region in order to showcase connectivity both within and between regions. To select ROIs for graph analyses, a set of parcels spanning the entire cerebral cortex was generated for each participant, and each parcel was assigned to one of 17 canonical functional networks using a graph theory-based community detection algorithm. Parcels and network assignments for subjects 1 and 2 were previously generated and published. We used identical methods for subject 3.

Functional Connectivity Measurement

Mean BOLD time series were extracted from each ROI by averaging the time series of all vertices within the ROI. Functional connectivity between ROIs was then measured for each session by computing the Pearson correlation between mean ROI BOLD time series, excluding high-motion frames. Daily time series of functional connectivity between ROIs are shown in FIGS. 6B, 6C, and 6D. Functional connectivity seed maps were computed for the left-hemisphere somatomotor cortex (L-SM1ue) ROI for each session by correlating the mean time series from the ROI with the time series from every voxel. Seed maps are shown in FIG. 6A.

Exponential Decay Model

The daily time course of functional connectivity between regions of interest (ROIs) was modeled using the following differential equation:

$$\frac{dr}{dt} = \propto (r_\infty - r)$$

$$r_\infty = \begin{cases} r_c \text{ if casted} \\ r_0 \text{ if not casted} \end{cases};$$

-continued $$\propto = \begin{cases} \propto_1 \text{ during casting} \\ \propto_2 \text{ during casting} \end{cases}$$

where r is the current functional connectivity between two ROIs, $r_0$ is the baseline functional connectivity, $r_c$ is the equilibrium functional connectivity in the casted state, $\propto_1$ describes the rate of change during the cast period and $\propto_2$ describes the rate of change during the post period. $r_0$ was set to the mean functional connectivity in the pre period. The other three parameters ($r_c$, $\propto_1$ and $\propto_2$) were fit to the data using a least-squares approach.

Total change in functional connectivity ($\Delta r$) reported in FIGS. 6B, 6C, and 6D, was computed as the difference between the modeled functional connectivity (r) at the end of the cast period minus baseline functional connectivity ($r_0$). The significance of $\Delta r$ was evaluated via permutation resampling (see Statistical analyses, below).

Graph-Theoretic Analyses

Graph analyses were based on a set of cortical parcels (see ROI selection, above) that were assigned to the face, lower-extremity and upper-extremity somatomotor networks (SMN). We excluded any parcels that were located outside of the pre- and post-central gyri. The resulting set of ROIs for each participant are shown in GS. 7A. Functional connectivity was computed for all pairs of somatomotor parcels and then averaged across sessions to produce a weighted graph of the SMN for each experimental period (Pre, Cast, Post). Thresholded graphs (FC>0.3) were displayed as spring-embedded plots (GS. 7B). Next, we computed for each graph. Modularity (GS. 7C) quantifies the extent to which different communities in a graph dissociate from one another. We defined two communities for computing modularity: 1) the casted upper extremity parcels (left-hemisphere parcels assigned to the upper-extremity SMN) and 2) the remainder of the SMN (bilateral lower-extremity and face SMN parcels and right-hemisphere upper-extremity SMN parcels). Thus, modularity reflects the degree of separation between the casted-extremity representation and the remainder of the SMN. Modularity (Q) is computed as:

$$Q = \frac{1}{2m}\sum_{ij}A_{ij} - \frac{k_ik_j}{2m}\delta(c_i, c_j)$$

where i and j are nodes in the graph, $A_{ij}$ is the connection strength between nodes i and j, $k_i$ and $k_j$ are the sums of all connection weights involving node i and node j, respectively, m is the sum of all connection weights in the graph, $c_i$ and $c_j$ are the community assignments of node i and node j, respectively, and $\delta$ is the Kronecker delta function (1 if $c_i$ and $c_j$ are identical and zero otherwise). Statistical significance of changes in modularity were evaluated using permutation resampling.

Figures 8A, 8B:
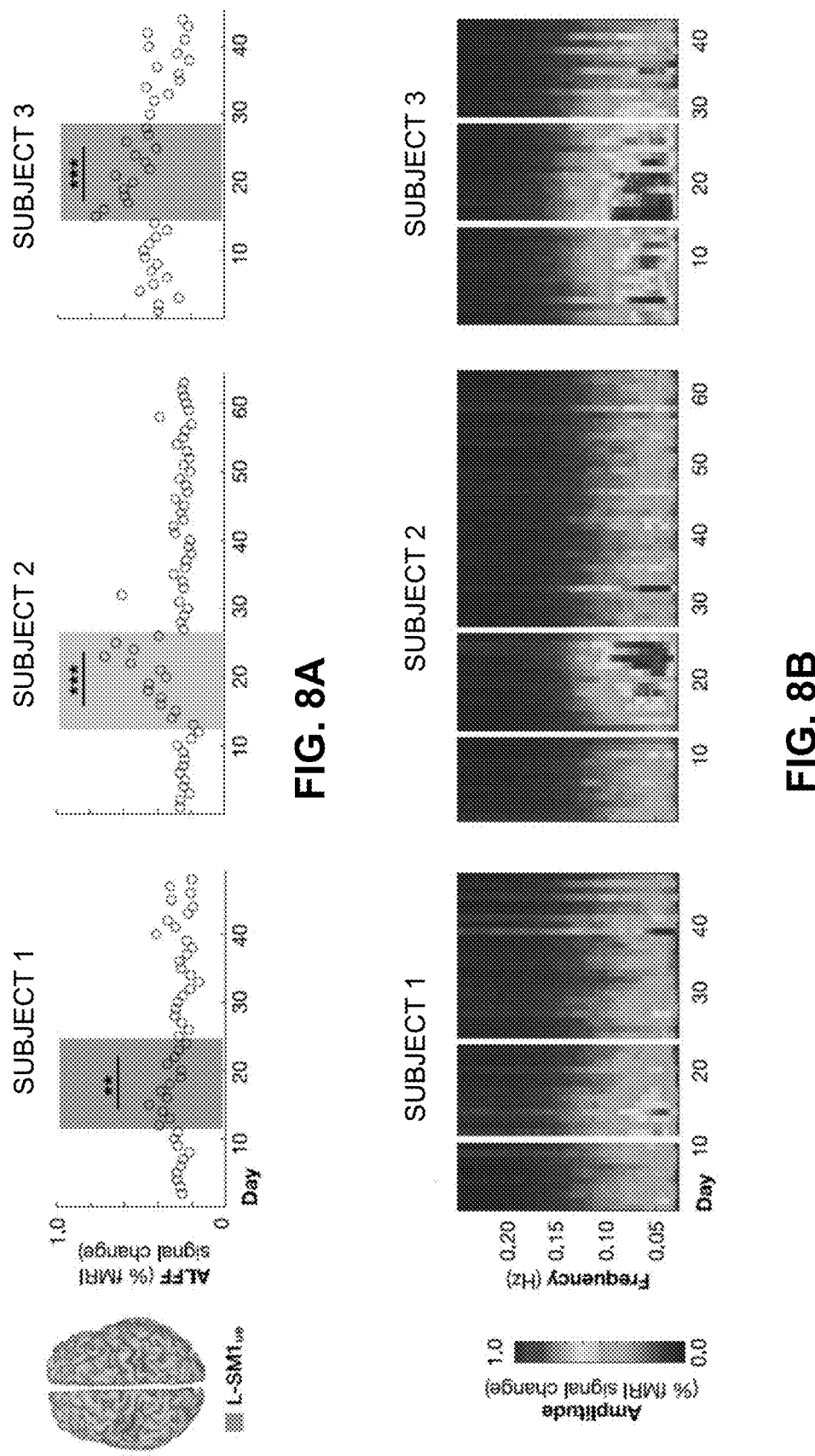
FIG. 8A contains a series of graphs summarizing ALFF in resting-state functional MRI (rs-fMRI) signals recorded from L-SM1ue on each day of an experiment. All participants showed significantly increased L-SM1ue ALFF during the cast period, relative to the pre period (Subject 1: +22%, p<0.01; Subject 2: +81%, p<0.001; Subject 3: +36%, p<0.001).
FIG. 8B contains the amplitude spectra of L-SM1ue rs-fMRI signals for the three subjects of FIG. 8A.

Spectral Analyses rs-fMRI signals from L-SM1ue and R-SM1ue were Fourier transformed to obtain amplitude density spectra. Spectra from all 30-minute scans in each participant are shown in FIG. 8B. Amplitude of low-frequency (ALFF) for L-SM1ue and R-SM1ue was calculated as the root mean square of amplitude across low frequencies (0.05-0.1 Hz). A daily time course of L-SM1ue and R-SM1ue ALFF for each participant is shown in FIGS. 8A, 8C, 8D, and 8E. ALFF during the cast period was compared to ALFF during the pre-period using an unpaired t test.

Pulse Detection

Example pulses were initially selected by visual inspection of L-SM1ue and R-SM1ue rs-fMRI signals. Based on these examples, threshold criteria were set to define pulses as large (>0.4% rs-fMRI signal change in L-SM1ue), unilateral (L-SM1ue minus R-SM1ue>0.3% rs-fMRI signal change) peaks in the L-SM1ue rs-fMRI signal. The number of pulses detected during each 30-minute rs-fMRI scan is shown in GS. 9C. To ensure that results did not depend on specific thresholds, we repeated all analyses using a range of thresholds (L-SM1ue>0.2% to 1.2% signal change; (L-SM1ue-R-SM1ue)>0.0% to 0.4% signal change). All thresholds yielded qualitatively similar results. Once pulses were detected in L-SM1ue, we used an analysis of variance (ANOVA) of whole-brain rs-fMRI signals surrounding each L-SM1ue pulse (13.2 s before to 17.6 s after each pulse peak) to determine if other brain regions showed consistent patterns of activity during pulses. Because the ANOVA F-statistic increases with increasing sample sizes, we divided by the square root of n (the number of pulses) to normalize maps across participants. The resulting maps are shown in FIG. 10A.

Pulse Timing Analyses

The exact timing of each pulse was estimated by temporally aligning each pulse event with the mean L-SM1ue pulse waveform. This alignment was implemented by parabolic optimization of the cross-correlation between each pulse event in each region of interest (L-SM1ue, L-SMAue, and R-Cblmue) and the mean pulse waveform. A similar approach was recently shown to provide reliable estimates of sub-TR time delays between rs-fMRI time series. FIG. 100 shows the relative time delays of pulse wave-forms extracted from L-SM1ue, L-SMAue, and R-Cblmue. Pulse times between regions were then compared using Wilcoxon signed rank tests.

Hand Movement Analyses

Pressure readings were acquired at 400 Hz. Pressure traces were low-pass filtered (<2 Hz) to remove high-frequency noise and differentiated to remove occasional shifts in baseline. The amplitude of pressure traces was normalized across recordings by dividing by the median deviation from the mean. Movements were detected by squaring the processed pressure trace, smoothing with a kernel of 1 s, and applying a threshold of 0.6. Disuse pulses detected in the rs-fMRI signals were classified as spontaneous if no movements were detected within 8 s preceding the pulse peak.

Statistical Analyses

All statistical tests were performed identically for each participant. Whenever appropriate, we used simple parametric statistical tests.

Accelerometry use counts measured during each day of the cast period (Subject 1: n=13 days; Subject 2: n=14; Subject 3: n=14) were compared to use counts during the pre period (Subject 1: n=7; Subject 2: n=14; Subject 3: n=14) using a two-sided, unpaired t test (Subject 1:

d.f.=18; Subject 2: d.f.=26; Subject 3: d.f.=26). This test was performed separately for each upper extremity.

Grip strength immediately after cast removal, measured in triplicate for each hand (all participants: n=3 measurements), was compared to all strength measurements acquired prior to casting (Subject 1: n=3; Subject 2: n=6; Subject 3: n=42) using a two-sided, un-paired t test (Subject 1: d.f.=4, Subject 2: d.f.=7, Subject 3: d.f.=43). This test was performed separately for each upper extremity (FIG. 5C).

d Performance on the Purdue pegboard task (#pegs inserted in 30 s) immediately after cast removal (all participants: n=3 trials), was compared to all trials conducted prior to casting (Subject 1: n=3; Subject 2: n=6; Subject 3: n=9) using a two-sided, un-paired t test (Subject 1: d.f.=4, Subject 2: d.f.=7, Subject 3: d.f.=10). This test was performed separately for each upper extremity.

To determine how quickly functional connectivity (FC) between the left and right somatomotor cortex (L-SM1ue and R-SM1ue) became significantly decreased in each participant, FC measured during each session of the cast period was compared to all sessions of the pre period (Subject 1: n=10 sessions; Subject 2: n=12; Subject 3: n=14) using two-sided, one-sample t tests (Subject 1: d.f.=9; Subject 2: d.f.=11; Subject 3: d.f.=13) conducted separately for each Cast session. We reported the time required for FC during a Cast session to become significantly lower (p<0.05) than FC during the pre-period.

Figures 8C, 8D:
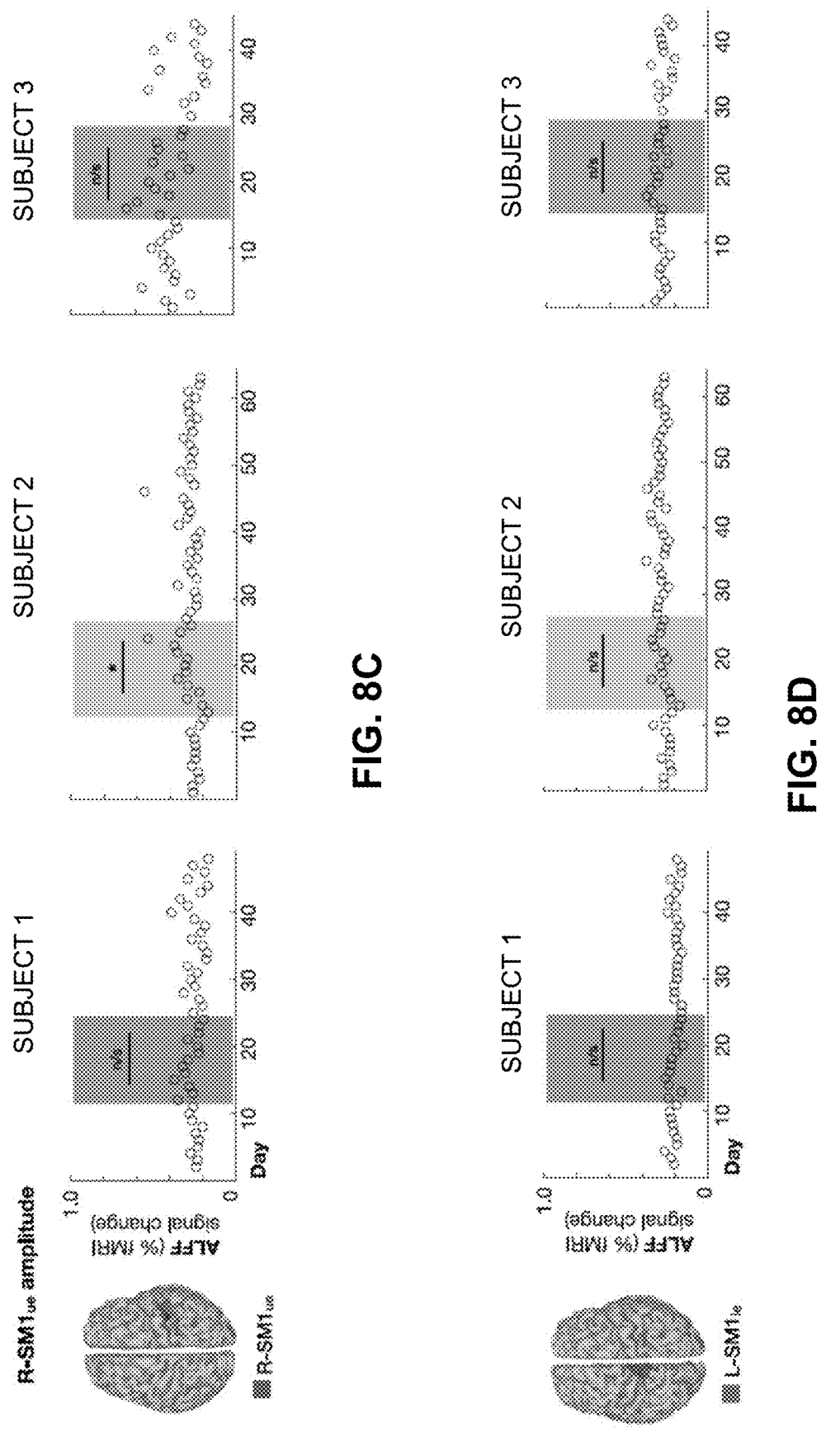
FIG. 8C contains a series of graphs summarizing the ALFF in R-SM1ue for the three subjects of FIG. 8A. Only Subject 2 showed significantly increased R-SM1ue ALFF during the cast period.
FIG. 8D contains a series of graphs summarizing the ALFF in lower-extremity somatomotor cortex (L-SM1le, negative control) for the three subjects of FIG. 8A. No subjects showed significant changes during the cast period.
Figure 8E:
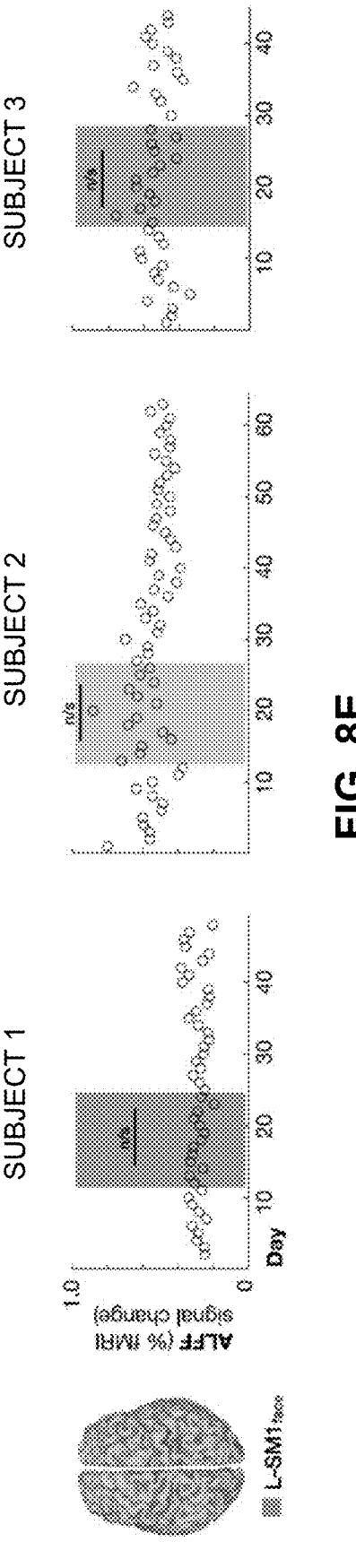
FIG. 8E contains a series of graphs summarizing the ALFF in ace somatomotor cortex (L-SM1face; negative control) for the three subjects of FIG. 8A. No subjects showed significant changes during the cast period.

Amplitude of low frequency fluctuations (ALFF) in L-SM1ue measured during each session of the cast period (Subject 1: n=13 sessions; Subject 2: n=13; Subject 3: n=14) was compared to ALFF measured during each session of the pre period (Subject 1: n=10; Ash-ley: n=12; Subject 3: n=14) using a two-sided, unpaired t test (Subject 1: d.f.=21, Subject 2: d.f.=23, Subject 3: d.f.=26). This test was repeated for R-SM1ue, L-SM1le, and L-SM1face (FIGS. 8C, 8D, and 8E).

The number of disuse pulses detected in L-SM1ue during each session of the cast period (Subject 1: n=13 sessions; Subject 2: n=13; Subject 3: n=14) was compared to the number of pulses detected during each session of the pre period (Subject 1: n=10; Subject 2: n=12; Subject 3: n=14) using a two-sided, unpaired t test (Subject 1: d.f.=21, Subject 2: d.f.=23, Subject 3: d.f.=26).

The relative timing of disuse pulses in L-SMAue and L-SM1ue was compared using a Wilcoxon signed rank test (Subject 1: d.f.=64, Subject 2: d.f.=143, Subject 3: d.f.=156). This test was repeated to compare the relative timing of disuse pulses in L-SMAue and R-Cblmue and the relative timing of disuse pulses in L-SM1ue and R-Cblmue (FIG. 100).

To evaluate the effects of wearing a removable cast during scanning, FC between L-SM1ue:R-SM1ue and L-Cblmue:R-Cblmue measured while participants wore removable casts ("On" sessions; Subject 1: n=6 sessions; Subject 2: n=12; Subject 3: n=6) was compared to sessions acquired without casts ("Off" sessions; Subject 1: n=6 sessions; Subject 2: n=12; Subject 3: n=6) using a two-sided un-paired t test (Subject 1: d.f.=10; Subject 2: d.f.=22; Subject 3: d.f.=10). The same test was used to compare the number of pulse-like events detected during On sessions to the number of events detected in Off sessions.

When parametric statistical tests were not appropriate to test a specific hypothesis, we tested results against a null distribution generated via permutation resampling. In each case, our null hypothesis was that no changes occurred due to casting and any observed differences were due to measurement error. We modeled this null hypothesis by permuting the order of MRI sessions 10,000 times, eliminating any temporal relationship between sessions and the casting intervention. Each permuted sample was treated exactly as the actual data in order to compute a null distribution for the value of interest. The P value reported for each test represents the two-sided probability that a value in the null distribution has a greater magnitude than the observed value. Per-mutation resampling was used to generate null distributions for the following values: change in functional connectivity ((Δr) during casting, based on the exponential decay model (FIGS. 6B. 6C, and 6D), and change in modularity of the somatomotor network (ΔQ) during casting (FIG. 7C).

All analyses were hypothesis driven and tested in a small number of regions of interest (ROIs), defined using independent data (task activations or baseline FC gradients). Correction for multiple comparisons was not necessary for most analyses. In cases where tests were applied to multiple ROIs, a Benjamini-Hochberg procedure was applied to correct for multiple comparisons, maintaining false discovery rates<0.05. This correction was applied to the following tests: decreases in homotopic FC, tested in three pairs of ROIs: L-SM1ue:R-SM1ue, R-Cblmue:L-Cblmue, and L-SMAue:R-SMAue; and delays in pulse timing, tested between three pairs of ROIs: L-SM1ue-→/R-Cblmue, L-SMAue→L-SM1ue, and L-SMAue→R-Cblmue.

Each of the three participants constituted a separate replication of the experiment, rather than multiple comparisons, so no correction was necessary for tests repeated in each participant.

Data Visualization

Regions of interest and whole-brain pulse maps were shown on cortical surfaces generated by FreeSurfer and Human Connectome Project (HCP) Workbench software packages. These images were rendered using HCP Workbench. All other figures were produced using MATLAB (https://www.mathworks.com/).

Results

Casting Caused Disuse and Reduced Strength of the Dominant Upper Extremity

Casts constrained movement of the elbow, wrist, and fingers. Accelerometers worn continuously on both wrists documented greatly reduced use of the casted upper extremity (FIG. 5B, use counts; Subject 1:–41%, Subject 2: –55%, Subject 3: –46%). Immediately after cast removal, participants showed reduced grip strength (FIG. 50, dynamometry; Subject 1:–27%, Subject 2:–42%, Subject 3:–39%) and reduced finemotor skill Purdue Pegboard; Subject 1: –24%, Subject 2:–29%, Subject 3:–12%). Participants showed increased use of the un-casted upper extremity (Subject 1: +24%, Subject 2: +15%, Subject 3: +23%) and reported subjective improvement in the use of this extremity during activities of daily, but they did not consistently show improvements in strength or fine motor skill (FIG. 5C).

Disused Somatomotor Regions Became Functionally Uncoupled from the Remainder of the Somatomotor System FC was originally discovered between the right upper-extremity primary somatomotor cortex (L-SM1ue) and the homotopic region of the opposite hemi-sphere (R-SM1ue). Prior to casting, all participants showed strong homotopic FC between L-SM1ue and R-SM1ue (FIGS. 6A and 6B). Casting led to a large reduction in FC between L-SM1ue and R-SM1ue in all participants (FIG. 6B; Subject 1: Δr=–0.23, Subject 2: Δr=–0.86, Subject 3: Δr=–0.61). We also found significantly decreased FC between the disused upper-extremity region of the cerebellum (R-Cblmue) and its homotopic counterpart (L-Cblmue, Subject 1: Δr=–0.16, Subject 2: Δr=–0.07, Subject 3: Δr=–0.33).

Decreased homotopic FC was somatotopically specific to the disused upper-extremity somatomotor cortex and cerebellum (L-SM1ue:R-SM1ue, R-Cblmue:L-Cblmue) and did not occur in lower-extremity (L-SM1le:R-SM1le, R-Cblmle:L-Cblmle) or face regions (L-SM1face:R-SM1face, R-Cblmface:L-Cblmface, FIGS. 6C and 6D). In all participants, FC decreases became significant within 48 h of casting (Subject 1: cast day 2 Δr=–0.22, p< 0.001; Subject 2: cast day 1 Δr=–0.23, p<0.001; Subject 3: cast day 1 Δr=–0.83, p<0.001). While disused regions in the somato-motor cortex and cerebellum (L-SM1ue and R-Cblmue) were functionally disconnected from the opposite hemisphere, these same regions became more connected to each other. The net effect was that disused brain regions dissociated from the remainder of the somatomotor system (FIG. 7B). All effects returned to baseline within days after cast removal (FIGS. 6B and 7C).

Figure 9B:
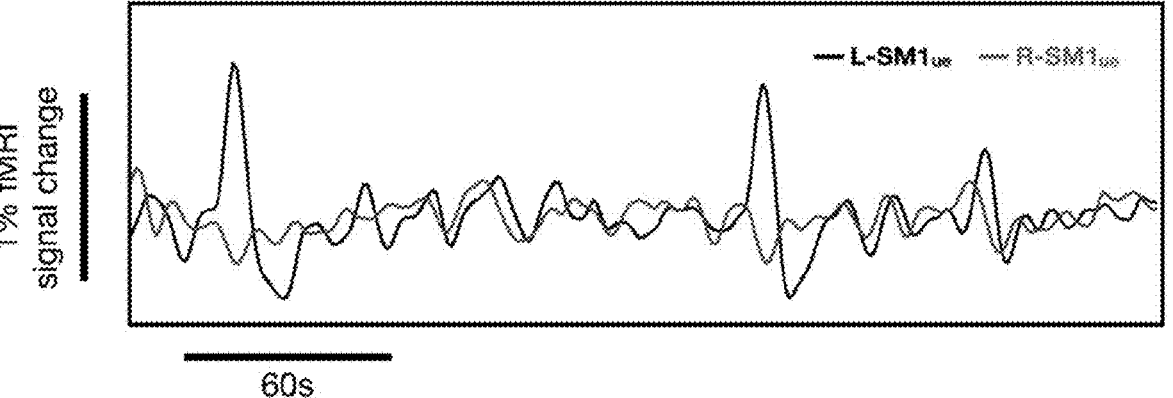
FIG. 9B is an enlarged view of the resting-state functional MRI (rs-fMRI) signals within the region bounded by the overlaid black rectangle of FIG. 9A.
Figure 9C:
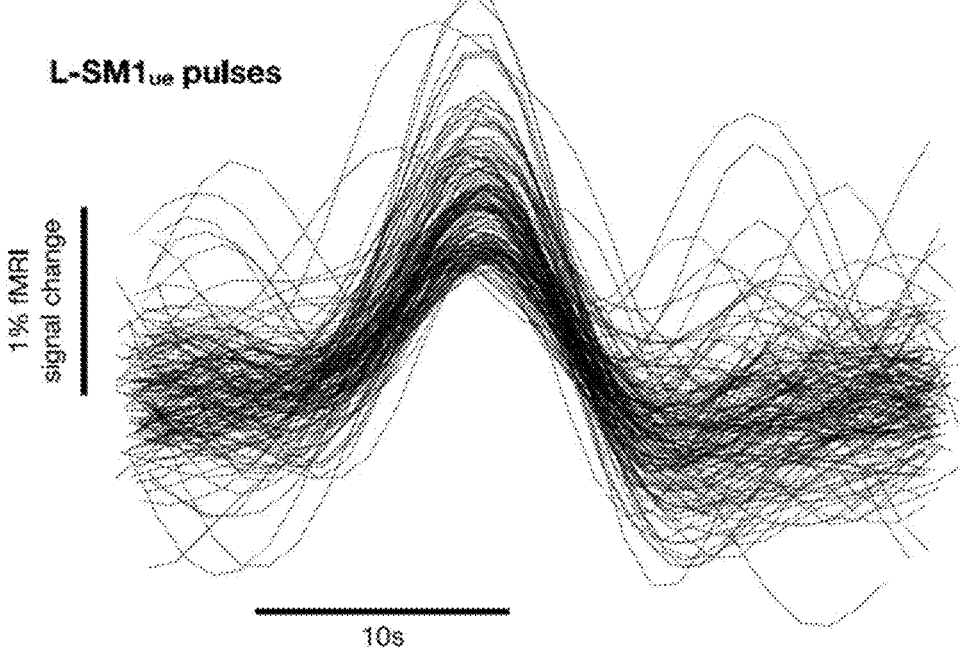
FIG. 9C is a graph showing the recordings of 144 disuse pulses detected from Subject 2.

Spontaneous Activity Pulses Emerged in the Disused Somatomotor Cortex During Casting To further characterize the changes in spontaneous activity caused by casting, we closely examined rs-fMRI signals in L-SM1ue and R-SM1ue. During the cast period, all participants showed significantly increased amplitude of low-frequency fluctuations (ALFF) in L-SM1ue (FIGS. 8A and 8B; Subject 1: +22%, Subject 2: +81%, Subject 3: +36%), and one participant showed increased ALFF in R-SM1ue (FIG. 8C, Subject 2: +26%). Increased ALFF was specific to the upper-extremity somatomo-tor cortex and did not occur in adjacent regions (L-SM1le and L-SM1face; FIGS. 8D and 8E). Unexpectedly, inspection of the rs-fMRI time series revealed large, spontaneous pulses of activity during the cast period (FIG. 9B). We termed these events "disuse pulses." The shape of disuse pulses (FIG. 9C) resembled the canonical hemodynamic response to a brief stimulus. Disuse pulses had a large amplitude (up to 1.5% signal change) and were easily distinguished from ongoing spontaneous fluctuations in L-SM1ue (<0.5% signal change; FIG. 9B). Pulses were essentially absent prior to casting (Subject 1: 1.1 pulses/scan; Subject 2: 0.2; Subject 3: 1.0), occurred frequently during the cast period (Subject 1: 4.2; Subject 2: 11.4; Subject 3: 12.3), and were infrequent after cast removal (Subject 1: 0.9; Subject 2: 0.8; Subject 3: 1.9; FIG. 9D).

Disuse Pulses Propagated Through the Disused Somatomotor Sub-Circuit

Disuse pulses were not only present in L-SM1ue but propagated throughout the disused upper-extremity subcircuit, i.e., L-SM1ue, L-SMAue, and R-Cblmue (FIG. 10A). A consistent pattern of pulse propagation was observed in all participants. Pulses sequentially occurred in L-SMAue, L-SM1ue, and then R-Cblmue, with mean time delays of approximately 200 and 600 ms, respectively (FIGS. 10B and 10C). This sequence of temporal lags is similar to that found in ongoing spontaneous activity. Monitoring of upper-extremity movements in one participant (Subject 3), using a highly sensitive pressure bladder placed inside the cast, showed that most pulses occurred in the absence of movements. To verify that spontaneous activity changes observed during the cast period were due to disuse during daily life rather than the presence of casts during scanning, we conducted a control experiment in which participants wore removable casts only during 30-min scans. We found only minimal changes in FC and almost no pulse-like events, indicating that the large decreases in FC and numerous disuse pulses observed during the cast period were not driven by wearing a cast during scans.

Discussion

Disuse Drives Large Decreases in Functional Connectivity

The magnitude of FC changes induced by casting (Δr=–0.23,–0.86,–0.61) is noteworthy because FC is typically highly stable from day to day. By the end of the 2-week cast period, FC in all participants was as low as has been observed after motor stroke or limb amputation. Animal studies that pharmacogenetically manipulated specific brain regions were able to drive large changes in (Δr>0.3). Yet, prior human studies of experimentally induced plasticity found much smaller effects (Δr~0.1). Key differences between the current experiment and previous studies are: (1) use of a sustained behavioral intervention, (2) inducing disuse as opposed to training a skill, (3) measuring daily time courses rather than comparing only pre/post, (4) overcoming sampling variable with longer (30-min) scans, and (5) conducting analyses at the level of individual participants, enabling 3-fold replication of all major findings.

Functional Connectivity can Change Rapidly Over a Span of Days

The observed loss of homotopic FC during disuse, corroborated by animal models of visual deprivation and deafferentation, supports the hypothesis that FC can be strengthened by coactivation of brain regions. The interval over which the effects of coactivation are accumulated was previously unknown. Some have suggested that patterns of coactivation are accumulated over many. However, the current results demonstrate that FC can be significantly altered within 12-48 hours when a sufficiently strong behavioral constraint is imposed, suggesting that FC is determined, at least in part, by a person's recent behaviors and experiences. The close relationship between FC and recent behavior raises the fascinating possibility that group differences in FC found in certain neuropsychiatric conditions, e.g., stroke, Parkinson's disease, Tourette syndrome, and limb amputation, may in part reflect disease-specific differences in day-to-day behavior.

Disused Sub-Circuits Maintain Internal Connectivity

In addition to disconnecting from the opposite hemisphere, disused regions (L-SM1ue and R-Cblmue) became more strongly connected to each other. Increased FC among disused regions has also been observed in mice during binocular deprivation. Disuse-driven increases in FC were not predicted by the Hebbian FC hypothesis. A straightforward Hebbian account would have predicted that disused regions should disconnect from all other regions. Rather, FC among disused regions (L-SM1ue and R-Cblmue) seems to have increased due to synchronized pulses of activity during the cast period.

Spontaneous Activity Shapes Neural Circuits during Development

The presence of spontaneous pulses in the disused somatomotor sub-circuit may reflect processes that help maintain the functional organization of the adult brain. Simultaneously, pulses may also have contributed to reductions in FC between the disused sub-circuit and the remainder of the somatomotor system. Spontaneous activity serves several known roles in shaping neural circuits. Hippocampal sharp-wave ripples and thalamic sleep spindles are thought to facilitate transfer of newly formed memories to the cortex. Moreover, large-amplitude transients at low frequencies, similar to the disuse pulses described here, are a hallmark feature of developing brains and help to shape brain-wide circuits in utero. In the developing visual system, spontaneous waves of activity originate in the retina and propagate through the entire visual system, helping to link circuits across several cortical and subcortical regions. Similar activity-dependent refinement of the somatomotor system is triggered by spontaneous activation of spinal motor neurons. The finding of disuse pulses in our participants suggests that adult brain circuits may retain a latent potential to self-organize through spontaneous activity. Spontaneous activity transients seen in development show a characteristic pattern of electrical activity, known as delta-brushes. Future experiments utilizing electroencephalography (EEG) in humans or microelectrode recording in animals will allow closer comparison of disuse pulses to spontaneous activity transients.

Focal Disinhibition May Allow for the Emergence of Spontaneous Activity Pulses

The disuse pulses observed in our participants were larger (up to 1.5% signal change) than the spontaneous activity fluctuations typically observed in the adult brain and may have resulted from disinhibition of disused circuits. During postnatal critical periods, inhibitory interneurons begin to suppress spontaneous activity, shifting the primary driver of activity-dependent plasticity from internal to external sources. Perhaps as a result of increased inhibitory tone, spontaneous activity in the adult brain does not typically include transients and is instead characterized by ongoing, stationary fluctuations. Disused circuits exhibit characteristic changes in local physiology: principal cells begin responding to previously silent inputs, inhibitory interneurons become less active, and the synapses between inhibitory interneurons and principal cells are weakened. Disuse-driven disinhibition may permit the reemergence of spontaneous pulses of activity in the adult brain. Indeed, pharmacogenetic suppression of inhibitory interneurons in the somatosensory cortex of adult mice produces spontaneous bursts of activity that propagate to functionally connected regions. Focal disinhibition is also thought to occur after stroke, another condition in which circuits are disused. An important question is whether disuse pulses arise during stroke recovery and how they impact clinical outcomes.

The Human Brain—Plastic Yet Stable

In the absence of regular use, our participants showed rapid loss of homotopic somatomotor FC. Thus, the human brain retains a surprising capacity for use-driven plasticity into adulthood. Simultaneously, large pulses of spontaneous activity began propagating through the disused somatomotor sub-circuit, helping to maintain its internal functional connectivity. Since somato-motor connectivity and motor performance returned to baseline quickly after cast removal, disuse pulses may have protected the integrity of the disused sub-circuit. Functional disconnection of disused sub-circuits, stabilized by spontaneous activity pulses, may allow the brain to reorganize itself rapidly without compromising its overall stability. Disuse pulses, analogous to waves of spontaneous activity seen during development, may allow the adult brain to bridge the seeming chasm between plasticity and stability.

What is claimed is:

1. A computer-implemented method of monitoring neuroplasticity within at least one resting state functional network of a brain of a subject, the method comprising:

a. obtaining a plurality of time sequences of signals from the brain of a subject in the absence of stimuli, each of the plurality of time sequences of signals comprising a plurality of pulses, each pulse of the plurality of pulses comprising a peak amplitude, wherein the at least one time sequence of signals is indicative of resting state neuroactivity within at least one resting state functional network within the brain of the subject;

b. receiving, using a computing device, the plurality of time sequences of signals;

c. projecting, using the computing device, the plurality of time sequences of signals to a 2D cortex model comprising a plurality of vertices mapped to cortical positions of the subject;

d. identifying, using the computing device, functionally connected regions corresponding to resting state functional networks by pair-wise evaluating Pearson correlations between the plurality of time sequences of signals;

e. identifying, using the computing device, a plurality of plasticity pulses, each plasticity pulse comprising a large amplitude signal pulse and a unilateral signal pulse, wherein each plasticity pulse of the plurality of plasticity pulses is identified by:

i. comparing, using the computing device, the peak amplitude of one pulse of the plurality of pulses to a constant threshold amplitude and classifying, using the computing device, the one pulse as large amplitude if the peak amplitude is above the constant threshold amplitude; and ii. obtaining, using the computing device, a peak difference comprising a difference between the peak amplitude of the one pulse and a corresponding contralateral peak amplitude of a contralateral pulse, wherein the peak amplitude and the contralateral peak amplitude comprise matched signal acquisition times and correspond to contralateral positions within a single functionally connected region;

iii. comparing, using the computing device, the peak difference to a constant peak difference threshold and classifying, using the computing device, the one pulse as a unilateral if the peak difference is above the constant peak difference threshold; and iv. adding, using the computing device, the one pulse to the plurality of plasticity pulses if the one pulse is classified as large amplitude and unilateral;

f. transforming, using the computing device, the plurality of plasticity pulses into a summary parameter indicative of the presence of plasticity pulses, the summary parameter comprising at least one of: a production rate of plasticity pulses, a mean amplitude of plasticity pulses, an amplitude of low frequency fluctuations, and any combination thereof;

g. generating, using the computing device, a determination of neuroplasticity based on the summary parameter; and h. displaying, using the computing device, the determination of neuroplasticity to a clinical practitioner, wherein the determination of neuroplasticity comprises at least one of a presence of neuroplasticity, a magnitude of neuroplasticity, and a spatial extent of neuroplasticity within the brain of the subject.

2. The method of claim 1, wherein each of the at least one resting state functional networks is selected from a dorsal attention network (DAN), a ventral attention network (VAN), a cingulo-opercular network (CO), a somato-motor network (SMN), an auditory network (AN), a visual network (VIS), a frontoparietal control network (FPC), a language network (LAN), and a default mode network (DMN).

3. The method of claim 1, wherein the at least one plurality of time sequences of signals comprises one of resting-state functional MRI (rs-fMRI) signals, electroencephalography (EEG) recordings, and microelectrode recordings.

4. The method of claim 1, wherein the constant threshold amplitude comprises a first constant value selected from a range between about a 0.2% signal change and about a 1.2% signal change from a baseline signal level.

5. The method of claim 4, wherein the constant threshold peak difference comprises a second constant value selected from a second range between about a 0.1% signal change to about a 0.4% signal change from a baseline signal level.

6. A computer-implemented method of evaluating an efficacy of a neuroactive therapy, the method comprising:

a. obtaining, using a computing device, a pre-treatment determination of neuroplasticity prior to administration of a neuroactive therapy;

b. obtaining, using the computing device, at least one post-treatment determination of neuroplasticity at least once after administration of the neuroactive therapy; and c. determining, using the computing device, the efficacy of the neuroactive therapy based on the pretreatment determination of neuroplasticity and the at least one post-treatment determination of neuroplasticity, wherein the efficacy of the neuroactive therapy is proportional to an increase in post-treatment neuroplasticity relative to pre-treatment neuroplasticity;

wherein obtaining the pre-treatment and post-treatment determinations of neuroplasticity comprise:

i obtaining a plurality of time sequences of signals from the brain of a subject in the absence of stimuli, each of the plurality of time sequences of signals comprising a plurality of pulses, each pulse of the plurality of pulses comprising a peak amplitude, wherein the at least one time sequence of signals is indicative of resting state neuroactivity within at least one resting state functional network within the brain of the subject;

ii. receiving, using the computing device, the plurality of time sequences of signals;

iii. projecting, using the computing device, the plurality of time sequences of signals to a 2D cortex model comprising a plurality of vertices mapped to cortical positions of the subject;

iv. identifying, using the computing device, functionally connected regions corresponding to resting state functional networks by pair-wise evaluating Pearson correlations between the plurality of time sequences of signals;

v. identifying, using the computing device, a plurality of plasticity pulses, each plasticity pulse comprising a large amplitude signal pulse and a unilateral signal pulse, wherein each plasticity pulse of the plurality of plasticity pulses is identified by:

1) Comparing, using the computing device, the peak amplitude of one pulse of the plurality of pulses to a constant threshold amplitude and classifying, using the computing device, the one pulse as large amplitude if the peak amplitude is above the constant threshold amplitude;

2) obtaining, using the computing device, a peak difference comprising a difference between the peak amplitude of the one pulse and a corresponding contralateral peak amplitude of a contralateral pulse, wherein the peak amplitude and the contralateral peak amplitude comprise matched signal acquisition times and, correspond to contralateral positions within a single functionally connected region;

3) comparing, using the computing device, the peak difference to a constant peak difference threshold and classifying, using the computing device, the one pulse as a unilateral if the peak difference is above the constant peak difference threshold; and 4) Adding, using the computing device, the one pulse to the plurality of plasticity pulses if the one pulse is classified as large amplitude and unilateral; and vi. transforming, using the computing device, the plurality of plasticity pulses into a summary parameter indicative of the presence of plasticity pulses, the summary parameter comprising at least one of: a production rate of plasticity pulses, a mean amplitude of plasticity pulses, an amplitude of low frequency fluctuations, and any combination thereof; and vii. generating, using the computing device, the determination of neuroplasticity based on the summary parameter.

7. The method of claim 6, wherein the neuroactive therapy is selected from a neuroactive medication, a physical therapy, an occupational therapy and a speech therapy.

8. A computer-implemented method of screening a neuroactive medication for use in a therapy, the method comprising:

a. obtaining, using a computing device, a pre-treatment determination of neuroplasticity prior to administration of the neuroactive medication to a subject;

b. obtaining, using the computing device, at least one post-treatment determination of neuroplasticity at least once after administration of the neuroactive medication to the subject; and c. selecting, using the computing device, the neuroactive medication for a therapy if the at least one post-treatment determination of neuroplasticity indicates higher neuroplasticity relative to the pre-treatment determination of neuroplasticity;

wherein obtaining the pre-treatment and post-treatment determinations of neuroplasticity comprise:

i. obtaining a plurality of time sequences of signals from the brain of a subject in the absence of stimuli, each of the plurality of time sequences of signals comprising a plurality of pulses, each pulse of the plurality of pulses comprising a peak amplitude, wherein the at least one time sequence of signals is indicative of resting state neuroactivity within at least one resting state functional network within the brain of the subject;

ii. receiving, using the computing device, the plurality of time sequences of signals;

iii. receiving, using the computing device, the plurality of at least one time sequences of signals;

iv. identifying, using the computing device, functionally connected regions corresponding to resting state functional networks by pair-wise evaluating Pearson correlations between the plurality of time sequences of signals;

v. identifying, using the computing device, a plurality of plasticity pulses, each plasticity pulse comprising a large amplitude signal pulse and a unilateral signal pulse, wherein each plasticity pulse of the plurality of plasticity pulses is identified by:

1) Comparing, using the computing device, the peak amplitude of one pulse of the plurality of pulses to a constant threshold amplitude and classifying, using the computing device, the one pulse as large amplitude if the peak amplitude is above the constant threshold amplitude;

2) obtaining, using the computing device, a peak difference comprising a difference between the peak amplitude of the one pulse and a corresponding contralateral peak amplitude of a contralateral pulse, wherein the peak amplitude and the contralateral peak amplitude comprise matched signal acquisition times and, correspond to contralateral positions within a single functionally connected region;

3) Comparing, using the computing device, the peak difference to a constant peak difference threshold and classifying, using the computing device, the one pulse as a unilateral if the peak difference is above the constant peak difference threshold;

4) Adding, using the computing device, the one pulse to the plurality of plasticity pulses if the one pulse is classified as large amplitude and unilateral; and vi. transforming, using the computing device, the plurality of plasticity pulses into a summary parameter indicative of the presence of plasticity pulses, the summary parameter comprising at least one of: a production rate of plasticity pulses, a mean amplitude of plasticity pulses, an amplitude of low frequency fluctuations, and any combination thereof; and vii. generating, using the computing device, the determination of neuroplasticity based on the summary parameter.

9. A computer-implemented method of providing a biofeedback to a subject undergoing a neuroactive therapy, the method comprising:

a. monitoring, using a computing device, a determination of neuroplasticity during administration of the neuroactive therapy to the subject, wherein the determination of neuroplasticity is obtained by:

i. obtaining a plurality of time sequences of signals from the brain of a subject in the absence of stimuli, each of the plurality of time sequences of signals comprising a plurality of pulses, each pulse of the plurality of pulses comprising a peak amplitude, wherein the at least one time sequence of signals is indicative of resting state neuroactivity within at least one resting state functional network within the brain of the subject;

ii. receiving, using the computing device, the plurality of sequences of signals;

iii. projecting, using the computing device, the plurality of time sequences of signals to a 2D cortex model comprising a plurality of vertices mapped to cortical positions of the subject;

iv. identifying, using the computing device, functionally connected regions corresponding to resting state functional networks by pair-wise evaluating Pearson correlations between the plurality of time sequences of signals;

v. identifying, using the computing device, a plurality of plasticity pulses, each plasticity pulse comprising a large amplitude signal pulse and a unilateral signal pulse, wherein each plasticity pulse of the plurality of plasticity pulses is identified by:

1) Comparing, using the computing device, the peak amplitude of one pulse of the plurality of pulses to a constant threshold amplitude and classifying, using the computing device, the one pulse as large amplitude if the peak amplitude is above the constant threshold amplitude;

2) obtaining, using the computing device, a difference between the peak amplitude of the one pulse and a corresponding contralateral peak amplitude of a contralateral pulse, wherein the peak amplitude and the contralateral peak amplitude comprise matched signal acquisition times and, correspond to contralateral positions within a single functionally connected region;

3) Comparing, using the computing device, the peak difference to a constant peak difference threshold and classifying, using the computing device, the one pulse as a unilateral if the peak difference is above the constant peak difference threshold; and 4) Adding, using the computing device, the one pulse to the plurality of plasticity pulses if the one pulse is classified as large amplitude and unilateral; and vi. transforming, using the computing device, the plurality of plasticity pulses into a summary parameter indicative of the presence of plasticity pulses, the summary parameter comprising at least one of: a production rate of plasticity pulses, a mean amplitude of plasticity pulses, an amplitude of low frequency fluctuations, and any combination thereof; and vii. generating, using the computing device, the determination of neuroplasticity based on the summary parameter; and b. displaying, using the computing device, the determination of neuroplasticity to the subject as the biofeedback.

* * * * *